United States Patent
Burke et al.

(10) Patent No.: US 11,524,132 B2
(45) Date of Patent: Dec. 13, 2022

(54) ADJUSTABLE AMBIENT AIR-OXYGEN BLENDER

(71) Applicant: Vayu Global Health Innovations, LLC, Medford, MA (US)

(72) Inventors: Thomas Friedrich Burke, Medford, MA (US); Anuj Bellare, Brighton, MA (US); Kamyar Mollazadeh Moghaddam, Cambridge, MA (US)

(73) Assignee: Vayu Global Health Innovations, LLC, Medford, MA (US)

( * ) Notice: Subject to any disclaimer, the term of this patent is extended or adjusted under 35 U.S.C. 154(b) by 357 days.

(21) Appl. No.: 15/985,985

(22) Filed: May 22, 2018

(65) Prior Publication Data

US 2018/0333555 A1     Nov. 22, 2018

Related U.S. Application Data

(60) Provisional application No. 62/509,292, filed on May 22, 2017.

(51) Int. Cl.
| | | |
|---|---|---|
| *A61M 16/10* | (2006.01) | |
| *A61M 16/12* | (2006.01) | |
| *A61M 16/20* | (2006.01) | |
| A61M 16/08 | (2006.01) | |
| A61M 16/00 | (2006.01) | |

(52) U.S. Cl.
CPC ........ *A61M 16/101* (2014.02); *A61M 16/106* (2014.02); *A61M 16/1065* (2014.02); *A61M 16/125* (2014.02); *A61M 16/127* (2014.02); *A61M 16/201* (2014.02); *A61M 16/022* (2017.08); *A61M 16/0875* (2013.01); *A61M 2202/0208* (2013.01)

(58) Field of Classification Search
CPC .............. A61M 16/101; A61M 16/106; A61M 16/1065; A61M 16/12; A61M 16/122; A61M 16/125; A61M 16/127
See application file for complete search history.

(56) References Cited

U.S. PATENT DOCUMENTS

| | | |
|---|---|---|
| 3,799,195 A | 3/1974 | Hermans |
| 4,235,229 A | 11/1980 | Ranford et al. |
| 4,929,238 A | 5/1990 | Baum |
| 5,116,088 A | 5/1992 | Bird |
| 7,191,780 B2 | 3/2007 | Faram |

(Continued)

FOREIGN PATENT DOCUMENTS

| | | |
|---|---|---|
| CN | 201350273 Y | 11/2009 |
| CN | 204840566 U | 12/2015 |

(Continued)

OTHER PUBLICATIONS

EPO, "Partial Supplementary European Search Report", EP18805098.3, dated Jun. 30, 2020.

(Continued)

*Primary Examiner* — LaToya M Louis
(74) *Attorney, Agent, or Firm* — Intrinsic Law Corp.

(57) ABSTRACT

An apparatus having an adjustable ambient air-oxygen blender that adjustably mixes ambient air with an oxygen supply, especially where a size, diameter or flow rate of an orifice is mechanically adjustable so as to control a quantitative mixing function of the blender.

6 Claims, 20 Drawing Sheets

(56) References Cited

U.S. PATENT DOCUMENTS

| | | |
|---|---|---|
| 7,562,659 B2 | 7/2009 | Matarasso |
| 9,132,250 B2 | 9/2015 | Allum et al. |
| 2005/0199237 A1 | 9/2005 | Lurie |
| 2009/0183739 A1 | 7/2009 | Wondka |
| 2011/0094518 A1 | 4/2011 | Cipollone et al. |
| 2015/0068519 A1 | 3/2015 | Bambrilla et al. |
| 2017/0151402 A1* | 6/2017 | Belisario ............. A61M 16/202 |
| 2017/0333661 A1* | 11/2017 | Bennett ............. A61M 16/0006 |
| 2018/0110954 A1* | 4/2018 | Belisario ............. A61M 16/101 |
| 2019/0094206 A1* | 3/2019 | Blomquist ....... A63B 21/00196 |

FOREIGN PATENT DOCUMENTS

| | | |
|---|---|---|
| EP | 0261649 A2 | 3/1988 |
| FR | 1068139 A | 6/1954 |
| WO | WO2016097669 A1 | 6/2016 |

OTHER PUBLICATIONS

Chaurette, J., "Unusual Aspects of Pump Systems", www.lightmypump.com, Jul. 2003, pp. 1-24.

ISA, "International Search Report", PCT/US2018/033835, dated Aug. 2, 2018.

CIPO, "Requisition by the Examiner", CA Application No. 3,061,193, dated Apr. 26, 2021.

* cited by examiner

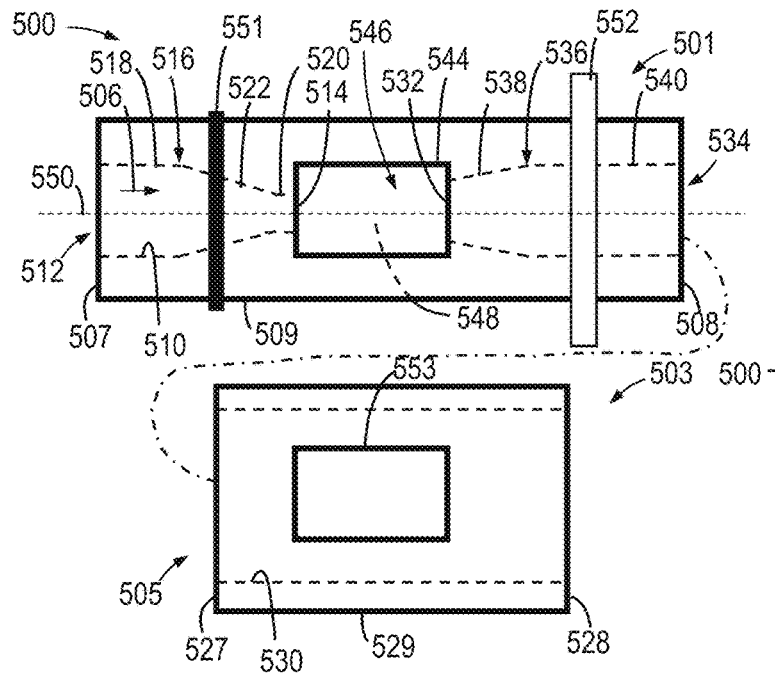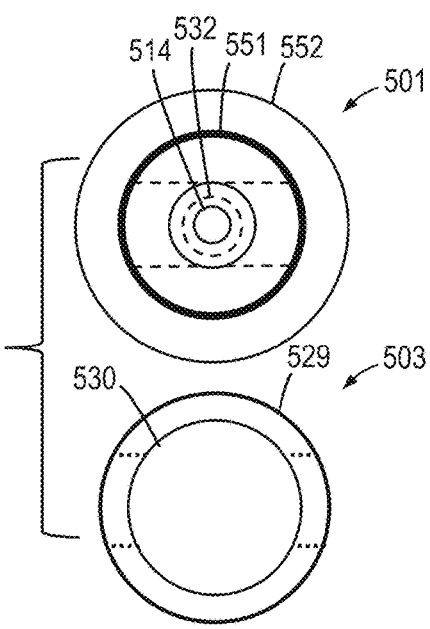
*FIG. 5A*
*FIG. 5D*
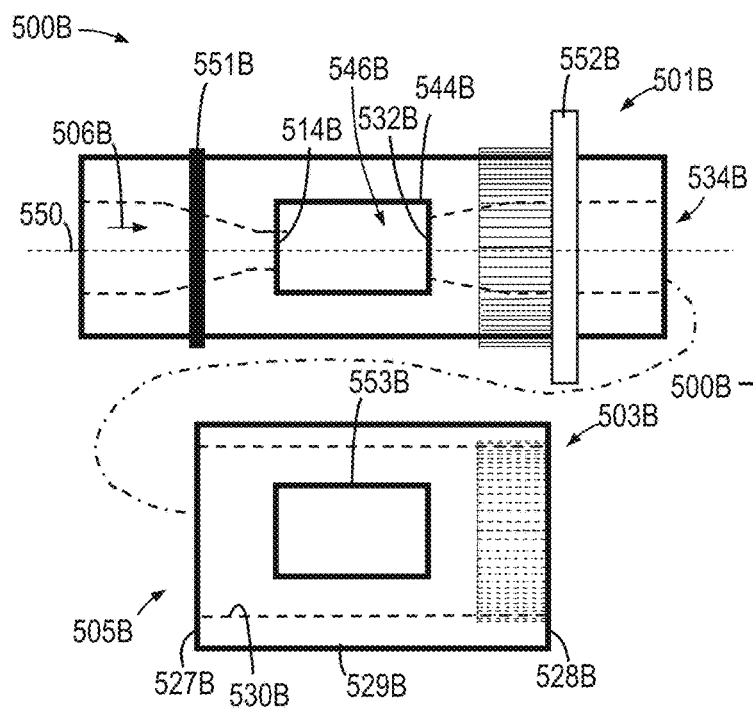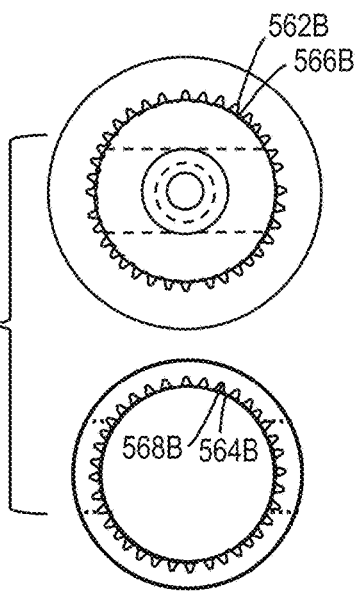
*FIG. 5B*
*FIG. 5E*

ADJUSTABLE AMBIENT AIR-OXYGEN BLENDER

RELATED APPLICATIONS

The present application claims the benefit of and priority to U.S. Provisional Application No. 62/509,292, filed on May 22, 2017, entitled "An Adjustable Ambient Air-Oxygen Blender," which is incorporated by reference herein in its entirety.

TECHNICAL FIELD

The present disclosure relates to modular ambient air-oxygen blending devices, whose design enables the user to change the oxygen content delivered without removal and replacement with a new blender, and to methods of fabrication.

BACKGROUND

Continuous positive airway pressure (CPAP) devices are effective in providing oxygen therapy for newborns with respiratory distress, over three million of whom die each year before 28 days of life, and several of them become disabled due to oxygen deprivation. In a hospital setting, it is possible to connect tubes from a tank of air and a tank of oxygen to provide a mixture of air and oxygen, which is generally necessary since 100% oxygen is associated with damage to the eye, brain and other organs. A pulse oximeter is used to monitor the fraction of inspired oxygen (FIO2) by the patient. In hospital settings especially in urban areas, CPAP devices that require electric power, either via connection to an electric wall socket or to a battery, are able to control the applied pressure of oxygen to the patient. Such devices are expensive and difficult to transport due to the weight of the air tank, oxygen tank, the pump based CPAP with pressure control and accessories. Furthermore, there is a need for electric power to operate these devices.

Bubble CPAPs (bCPAPs) overcome the need for electricity or a tank of air since the positive airway pressure is provided by breathing into a bottle containing water (bubbler) with the tube containing the expired air maintained at a known depth in the water. The water-depth of the exiting expired air from the patient controls the amount of back pressure to assist in respiration. A second advantage of such bCPAPs is that they don't use an air tank to produce a blend of air and oxygen to the patient, but instead use ambient air, which enters the oxygen stream through air entrainment ports of a device referred to as an ambient air-oxygen blender.

FIGS. 1A-1B are schematic views of a prior art ambient air-oxygen blender 100, which includes an oxygen tube 102 (on its left side), which has an inlet 104 (to receive a flow of oxygen) and a decreasing diameter 106. Referring now to FIGS. 1A-1B, the oxygen enters the blender 100, via the inlet 104 of the oxygen tube 102, and the oxygen exits the oxygen tube 102 at a high velocity via a small diameter nozzle 108 into an ambient air entrainment chamber 110, which has ports 112 to allow air 114 to blend into the oxygen. Thereafter, the mixture of air and oxygen enters an orifice 116, which usually has a larger diameter than the nozzle 108 of the oxygen tube 102, exits the blender 100 from an outlet 118 (on the right side 120 of the blender 100) and enters exit tubing (not shown in FIG. 1) that leads toward the mask of a patient (not shown in FIG. 1). This design utilizes the well-known Venturi effect according to which the velocity of a gas with a fixed flow rate increases when it goes through a contraction in the tubing and, as a result, the pressure decreases per Bernoulli's principle. FIG. 2 is a schematic view 200 showing that oxygen with a velocity, $V_1$ and Pressure $P_1$ entering a chamber 202 which narrows in diameter so that it exits a nozzle at a velocity $V_2$ and Pressure $P_2$, wherein according to Bernoulli's principle, $P_2-P_1=(\rho/2)(V_2^2-V_2^2)$.

The low-pressure in the air entrainment chamber 110, through which oxygen flows at a high velocity, creates a driving force to draw in ambient air 114. The relative fraction of air and oxygen then depends on the pressure drop, and consequently the velocity of the oxygen stream, which depends on the ratio of the diameter of the inlet tubing and the nozzle 108 diameter. The size of the air entrainment port 112 and the distance between the oxygen exit nozzle 108 and the entry orifice 116 through which the air-oxygen blend enters to be transported to the patient are also factors that affect the fraction of oxygen provided to the patient.

SUMMARY

Ambient air-oxygen blenders used in bCPAP devices are designed to blend a certain percentage of air into an oxygen stream emerging from an oxygen tank at a known flow rate. These blenders can be manufactured with different designs so that the distance between the exit nozzle of oxygen and the entry orifice (sometimes referred to herein as "the orifice," and sometimes referenced from an opposite perspective and referred to as "the exit orifice") for the blended air and oxygen at the opposite end of the air-entrainment chamber of the device are unique for each blender.

One of the disadvantages of the fixed geometry blender is that if the relative oxygen content to the patient in the air-oxygen mixture needs to be increased or decreased, the flow must be stopped, the blender dismantled, a new blender with a different design to provide a different fraction of oxygen must be connected, and the flow of oxygen can then be resumed. For example, if it is discovered that a patient needs a different fraction of oxygen than the amount provided by a particular ambient air-oxygen blender, the time lost during stoppage of the oxygen flow, dismounting the blender, mounting a new blender and resuming oxygen flow can result in respiratory distress for the patient and endanger their health. Furthermore, if it is discovered that the replacement blender is not sufficient for the patient and that a different fraction of oxygen is desired then this becomes a cumbersome task for the healthcare providers to repeat the tasks required to replace the blenders again, with considerably larger respiratory distress for newborns who are primary candidates for this therapy.

This is not an issue in settings that utilize a tank of air and oxygen for which valves can be used to adjust the relative flow rates of oxygen and air to change the ratio of air and oxygen delivered to a patient. However, in settings that utilize an ambient air-oxygen blender, a delay in replacing an ambient air-oxygen blender can cause unwanted respiratory distress to the patient. This disclosure provides various embodiments of modular ambient air-oxygen blending devices, whose design enables the user to change the oxygen content delivered without removal and replacement of the blender, and to methods of fabrication.

At least some of the adjustable ambient air-oxygen blenders disclosed herein allow the user to change the distance between the oxygen exit nozzle into the air entrainment port and the entry orifice of the air-oxygen mixture, which results in a change to the air-oxygen mixture, without dismounting the blender or stoppage of oxygen flow.

In one aspect, the adjustable ambient air-oxygen blender comprises two components, wherein the two components can be snugly fitted, screwed into each other or slid over ribs to adjust and lock their relative positions.

In another aspect, an adjustable blender is designed so that the cross-sectional area of the air-entrainment ports can be adjusted by using a collar.

In at least some embodiments, the adjustable ambient air-oxygen blender comprises a fixed ambient air-oxygen blender and a collar that can be rotated to cover the air entrainment ports to different extents, thereby controlling the amount of air that can blend into the oxygen stream passing through the air-entrainment chamber.

In one aspect, the adjustable ambient air-oxygen blender comprises an oxygen entry nozzle part (sometimes referred to herein as "entry nozzle piece") and a collar containing the exit orifice wherein the two parts fit snugly and their relative position can be changed by sliding the oxygen entry nozzle part back and forth.

In another aspect, the adjustable ambient air-oxygen blender comprises an oxygen entry nozzle part and a collar containing the exit orifice wherein both pieces contain ribs that allows the nozzle part to be inserted into the collar part and placed at various positions with respect to the ribs, which secure the relative location of the two pieces.

In another aspect, the adjustable ambient air-oxygen blender comprises an entry nozzle piece and a collar part (sometimes referred to herein as a "collar piece") containing the exit orifice wherein both parts contain threading to allow the nozzle piece to be rotated and screwed into the collar piece to change the relative location of the two parts.

In another aspect, the adjustable ambient air-oxygen blender comprises an entry nozzle part containing a collar. The adjustable ambient air-oxygen blender further comprises an exit orifice part (sometimes referred to herein as an "exit orifice piece") wherein the two parts fit snugly and their relative position can be changed by sliding the exit orifice part back and forth.

In another aspect, the adjustable ambient air-oxygen blender comprises an entry nozzle part having a collar containing ribs. The adjustable ambient air-oxygen blender further comprises an exit orifice that contains ribs to allow the exit orifice piece to be inserted into the collar and placed at various positions with respect to the ribs, which secure the relative location of the two pieces.

In another aspect, the adjustable ambient air-oxygen blender comprises an entry nozzle part having a collar containing threading. The adjustable ambient air-oxygen blender further comprises an exit orifice that contains threading to allow the exit orifice piece to be rotated and screwed into the collar to change the relative location of the two pieces.

In another aspect, the adjustable ambient air-oxygen blender comprises a fixed blender and a collar that slides over the fixed blender and fits snugly to it, which can be rotated to cover different areas of the air-entrainment ports of the blender.

In another aspect, apparatus comprises: an adjustable ambient air-oxygen blender comprising: an oxygen entry-nozzle piece defining: an oxygen inlet; and a nozzle in fluid communication with the oxygen inlet; an orifice piece movably coupled to the oxygen entry-nozzle piece and defining: an orifice in fluid communication with the nozzle of the oxygen entry-nozzle piece; and an oxygen-air mixture outlet in fluid communication with the orifice; and wherein the air-oxygen blender defines an ambient air entrainment port in fluid communication with the orifice of the orifice piece; wherein the nozzle of oxygen entry-nozzle piece and the orifice of the orifice piece are spaced apart by a variable distance; and wherein at least one of the oxygen entry-nozzle piece and the orifice piece is movable relative to the other to change the variable distance by which the nozzle of oxygen entry-nozzle piece and the orifice of the orifice piece are spaced apart.

In another aspect, apparatus comprises: an adjustable ambient air-oxygen blender defining: an oxygen inlet; a nozzle in fluid communication with the oxygen inlet; an orifice in fluid communication with the nozzle; an oxygen-air mixture outlet in fluid communication with the orifice; and an ambient air entrainment port in fluid communication with the orifice; the adjustable ambient air-oxygen blender comprising: an iris in fluid communication with the oxygen inlet.

In another aspect, the adjustable ambient air-oxygen blender comprises a fixed blender fabricated using a compliant material and a collar or belt that fits over the oxygen entry nozzle region wherein the collar can be tightened to decrease the diameter of the nozzle. The adjustable blender optionally includes a collar or belt over the exit orifice region which can be tightened or loosened to change the diameter of the exit orifice.

In another aspect, the components of the adjustable ambient air-oxygen blender is fabricated using thermoplastics, thermoplastic elastomers, elastomers, ceramics, metals, or a combination thereof.

In another aspect, the materials used in the fabrication of the adjustable ambient air-oxygen blender are compatible for use in a 3D printer to print such devices.

In another aspect, the adjustable ambient air-oxygen blender is fabricated by injection molding.

Embodiments of the adjustable ambient air-oxygen blenders include various combinations of the aspects described above.

Another embodiment is directed to an apparatus for blending an ambient gas and a supply gas to deliver a blended gas, the apparatus comprising an outer sleeve and an inner sleeve; wherein the outer sleeve has an ambient gas window described in its side for admitting said ambient gas into the apparatus, and the outer sleeve has an interior dimension being at least as large as an exterior dimension of said inner sleeve; wherein the inner and outer sleeves are mechanically couplable by insertion of the inner sleeve into the outer sleeve; wherein the inner sleeve is moveable with respect to the outer sleeve along an axis running through said inner and outer sleeves; wherein one of said sleeves defines a supply gas inlet at one of its ends, and the other one of said sleeves defines a blended gas outlet at one of its ends; and wherein moving the inner sleeve along said axis within the outer sleeve causes a corresponding occlusion of said ambient gas window so as to correspondingly vary a rate of entrainment of said ambient gas through the ambient gas window and correspondingly vary a fraction of said ambient gas in the blended gas delivered by said apparatus.

The sleeves may be substantially cylindrical, of circular, square or other cross sections, and slidably engage one another so that the overall length of the apparatus comprising the two-part body (sleeves) is elongated or reduced in length as the inner member (sleeve) slides out of or into the outer member (sleeve). The overall effect is a variable aperture or window that entrains ambient gas (e.g., air) from outside the apparatus into a flowing stream of supply gas (e.g., oxygen) from a supply inlet, to create a variable composition of blended (e.g., air-oxygen) gas exiting from an outlet of the apparatus.

This Summary is intended to provide an overview of at least some of the subject matter of the present disclosure. It is not intended to provide an exclusive or exhaustive explanation of the invention or embodiments thereof.

Thus, while certain aspects and embodiments have been presented and/or outlined in this Summary, it should be understood that the present aspects and embodiments are not limited to the aspects and embodiments in this Summary. Indeed, other aspects and embodiments, which may be similar to and/or different from, the aspects and embodiments presented in this Summary, will be apparent from the description, illustrations and/or claims, which follow.

While various features and/or advantages are described in this Summary and/or will become apparent in view of the following detailed description and accompanying drawings, it should be understood that such features and/or advantages are not required in all aspects and embodiments.

Any aspects and/or embodiments that are described in this Summary and do not appear in the claims that follow are preserved for later presentation in this application or in one or more continuation patent applications. Any aspects and/or embodiments that are not described in this Summary and do not appear in the claims that follow are also preserved for later presentation or in one or more continuation patent applications.

BRIEF DESCRIPTION OF THE DRAWINGS

It should be understood that the Figures described herein only provide illustrative embodiments of this invention and are not to be considered limiting of the scope of the invention since the invention may allow for other embodiments not included in these Figures.

FIG. 5A is a schematic side view of a fixed blender and a collar of an adjustable ambient air-oxygen blender shown in a disassembled state, in accordance with at least some embodiments;

FIG. 5B is a schematic side view of a fixed blender and a collar of an adjustable ambient air-oxygen blender shown in a disassembled state, in accordance with at least some embodiments;

FIG. 5D is a schematic end view of the fixed blender and the collar of the adjustable ambient air-oxygen blender of FIG. 5A shown in a disassembled state, in accordance with at least some embodiments;

FIG. 5E is a schematic end view of the fixed blender and the collar of the adjustable ambient air-oxygen blender of FIG. 5B shown in a disassembled state, in accordance with at least some embodiments;

DETAILED DESCRIPTION

As stated above, this invention provides various embodiments of modular ambient air-oxygen blending devices, whose design enables the user to change the oxygen content delivered without removal and replacement of the blender, and to methods of fabrication.

Figure 1A:
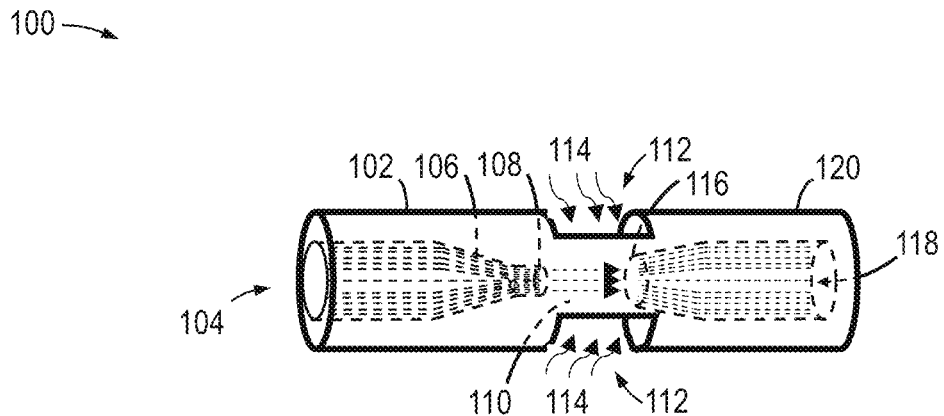
FIG. 1A is a schematic side view of a prior art ambient air-oxygen blender.
Figure 1B:
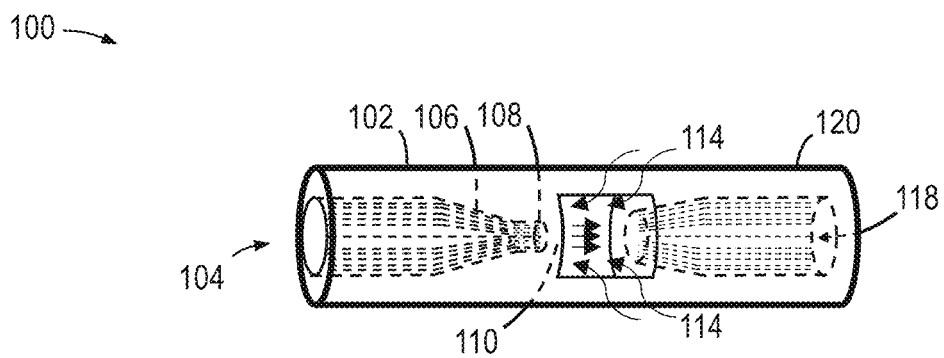
FIG. 1B is a schematic top view of the prior art ambient air-oxygen blender.
Figure 2:
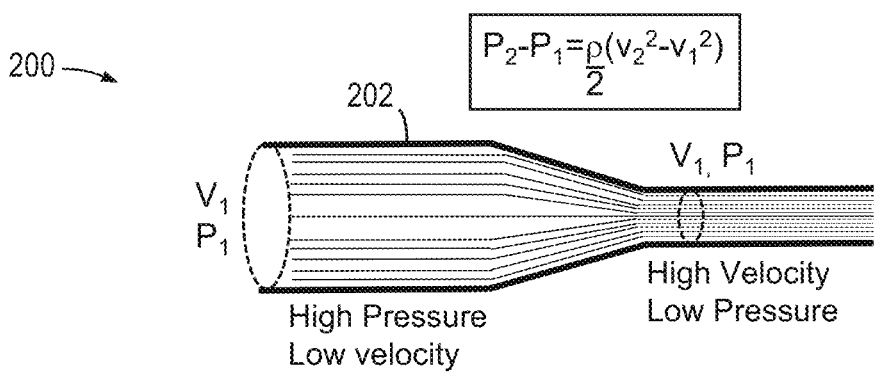
FIG. 2 is a schematic view of a prior art chamber.
Figure 3A:
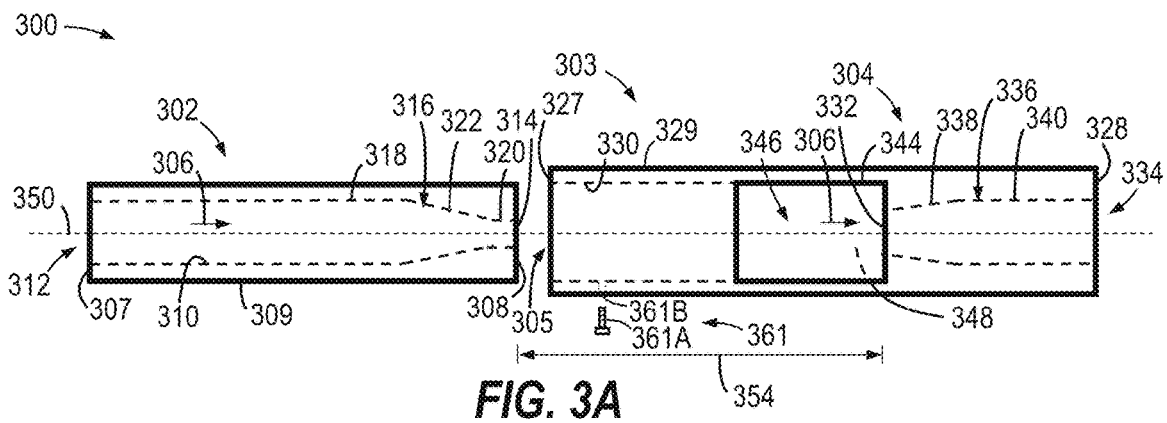
FIG. 3A is a schematic side view of an adjustable ambient air-oxygen blender in a disassembled state, in accordance with at least some embodiments.

FIG. 3A is a schematic side view showing an adjustable ambient air-oxygen blender 300 in a disassembled state, in accordance with at least some embodiments.

Referring now to FIG. 3A, in accordance with at least some embodiments, the adjustable ambient air-oxygen blender 300 includes an oxygen entry-nozzle piece 302 and an exit orifice piece 304 movably coupled thereto.

The adjustable ambient air-oxygen blender 300 may further include a collar 303 that movably couples the oxygen entry-nozzle piece 302 to the exit orifice piece 304. In the illustrated embodiment, the collar 303 includes the exit orifice piece 304, and as discussed below, may define an opening 305 to slidably or otherwise movably receive the oxygen entry-nozzle piece 302 to movably couple the oxygen entry-nozzle piece 302 and the exit orifice piece 304. In some other embodiments, a collar may instead be part of the oxygen entry-nozzle piece 302, and as discussed below, may define an opening to movably receive the exit orifice piece 304.

With the adjustable ambient air-oxygen blender 300 in an assembled state (i.e., with the oxygen entry-nozzle piece 302 and exit orifice piece 304 movably coupled to one another), the adjustable ambient air-oxygen blender 300 defines a gas flow path 306 that extends through the oxygen entry-nozzle piece 302 and the exit orifice piece 304.

The oxygen entry-nozzle piece 302 may have a first end 307, a second end 308, an outer surface 309 and an inner surface 310.

The oxygen entry-nozzle piece 302 defines an inlet 312, a nozzle 314 in fluid communication with the inlet 312, and a channel 316 extending between the inlet 312 and the nozzle 314. The inlet 312 may be disposed at the first end 307 of the oxygen entry-nozzle piece 302 and/or at a first end of the gas flow path 306. The nozzle 314, which may be disposed at the second end 308 of the oxygen entry-nozzle piece 302, is in fluid communication with and downstream of the inlet 312 and may have a cross sectional area that is less than a cross sectional area of the inlet 312. The channel 316 may have one or more spans of uniform cross-sectional diameter, e.g., a span 318 and a span 320, and/or one or more spans of decreasing cross sectional diameter, e.g., a span 322 having a uniformly decreasing or otherwise tapered contour.

The collar 303 and its exit orifice piece 304 may have a first end 327, a second end 328, an outer surface 329 and an inner surface 330. The exit orifice piece 304 defines an orifice 332 (sometimes referred to herein as an exit orifice), an oxygen-air mixture outlet 334 in fluid communication with the orifice 332, and a channel 336 extending between the orifice 332 and the oxygen-air mixture outlet 334. The orifice 332 is in fluid communication with and downstream of the nozzle 314 and may have a cross sectional area that is greater than the cross-sectional area of the nozzle 314. The oxygen-air mixture outlet 334, which may be disposed at a second end of the gas flow path 306, is downstream of the orifice 332 and may have a cross sectional area that is greater than the cross-sectional area of the orifice 332. The channel 336 may have one or more spans of increasing cross sectional diameter, e.g., a span 338 having a uniformly increasing or otherwise tapered contour, and/or one or more spans of uniform cross-sectional diameter, e.g., a span 340.

The adjustable ambient air-oxygen blender 300 defines at least one ambient air entrainment port, e.g., ambient air entrainment port 344, that provides at least one flow path, e.g., flow path 346, for ambient air to enter the adjustable ambient air-oxygen blender 300. In at least some embodiments, the at least one ambient air entrainment port, e.g., ambient air entrainment port 344, is defined at least in part by the oxygen entry-nozzle piece 302 and/or the collar 303. In the illustrated embodiment, the at least one ambient air entrainment port, e.g., ambient air entrainment port 344, is defined by the collar 303 (e.g., as shown). The at least one ambient air entrainment port, e.g., ambient air entrainment port 344, may have a rectangular cross section (e.g., as shown) or any other suitable configuration.

The adjustable ambient air-oxygen blender 300 may further define an ambient air entrainment chamber 348 in fluid communication with the nozzle 314 to receive oxygen that exits therefrom and in fluid communication with the at least one ambient air entrainment port, e.g., ambient air entrainment port 344, to receive ambient air that enters the adjustable ambient air-oxygen blender 300 therethrough. In at least some embodiments, including but not limited to the illustrated embodiment, the ambient air entrainment chamber 348 is disposed (at least in part) between the nozzle 314 and the orifice 332 and/or in fluid communication between the nozzle 314 and the orifice 332. In at least some embodiments, including but not limited to the illustrated embodiment, the ambient air entrainment chamber 348 is defined at least in part by the oxygen entry-nozzle piece 302 and/or the collar 303.

The adjustable ambient air-oxygen blender 300 may have a longitudinal axis 350, which may extend in a longitudinal direction. The oxygen entry-nozzle piece 302, the collar 303 and/or its exit orifice piece 304 may be disposed along and/or about the longitudinal axis 350 and/or may have a longitudinal axis coincident (or substantially coincident) with the longitudinal axis 350.

As used herein, the term "substantially coincident" means "coincident +/−10 degrees, preferably coincident +/−5 degrees, more preferably coincident +/−1 degree."

The flow path 306 (or one or more portions thereof) may be disposed along and/or about the longitudinal axis 350 and/or may have a longitudinal axis coincident (or substantially coincident) with the longitudinal axis 350.

As stated above, the collar 303 may define an opening 305 to slidably or otherwise movably receive the oxygen entry-nozzle piece 302 to movably couple the oxygen entry-nozzle piece 302 and the exit orifice piece 304. In at least some embodiments, including but not limited to the illustrated embodiment, the oxygen entry-nozzle piece 302 and collar 303 may have a snug fit wherein the two pieces 302, 303 fit snugly and their relative position can be changed, e.g., by sliding the entry nozzle piece 302 back and forth, as appropriate to achieve a desired change in relative position between the exit orifice piece 304 and the oxygen entry-nozzle piece 302.

The ability to change a relative positioning of the oxygen entry-nozzle piece 302 and the exit orifice piece 304 provides the ability to change a distance 354 (sometimes referred to herein as a variable distance 354) between the nozzle 314 and the orifice 332. The change in the variable distance 354 may be in a longitudinal (or at least substantially longitudinal) direction and/or in one or more other direction(s).

As used herein, the term "substantially longitudinal" means "longitudinal +/−10 degrees, preferably longitudinal +/−5 degrees, more preferably longitudinal +/−1 degree."

The change in the variable distance 354 results in a change to the air-oxygen mixture. The mixture is thus adjustable without any need to stop the flow of oxygen, dismantle a blender from the system, connect a new blender and then resume the flow of oxygen.

In at least some embodiments, the change in the relative positioning that results in the change in the variable distance 354 may result in a portion of the oxygen entry-nozzle piece 302 being disposed in line with at least a portion of the at least one air-entrainment port, e.g., the air entrainment port 344. This may reduce the amount of ambient air that enters the adjustable ambient air-oxygen blender 300 to mix into the flowing oxygen, which also results in a change to the air-oxygen mixture.

The snug fit may be a friction fit (a type of interference fit) in which the oxygen entry-nozzle piece 302 and collar 303 are pressed together and thereafter movably coupled by friction at the interface of the collar 303 and the oxygen entry-nozzle piece 302.

At least some embodiments may employ a friction fit of any desired tightness. As is known, the characteristics of a friction fit depend at least in part on the amount of dimensional interference that is provided at the interface between the two parts.

In at least some embodiments, a snug fit and/or a friction fit provides resistance to relative movement (longitudinal and/or rotational) between the collar 303 and oxygen entry-nozzle piece 302 to thereby movably couple and/or releasably secure the oxygen entry-nozzle piece 302 and the collar 303.

In at least some embodiments, the outer surface 309 of the oxygen entry-nozzle piece 302 and the inner surface 330 of the collar 303 may have a uniform (or at least substantially uniform) interface therebetween so as to permit a uniform or (at least substantially uniform) change in relative positioning upon application of uniform (or at least substantially uniform force) by a user (or otherwise) to the oxygen entry-nozzle piece 302 and/or the collar 303.

As used herein, the term "substantially uniform force" means "uniform force +/−10%, more preferably uniform force +/−5%, more preferably uniform force +/−1%".

In at least some embodiments, it may be desirable for a relative positioning to be maintained until it is determined that it is desirable to change such and appropriate force(s) are applied to do so. In at least some embodiments, a snug fit and/or friction fit may accomplish such at least to a desired extent.

In at least some embodiments, it may be desirable to further secure a relative positioning.

To that effect, in at least some embodiments, the adjustable ambient air-oxygen blender 300 may include a brake 361 (releasable or otherwise) to help prevent or otherwise reduce relative movement between the oxygen entry-nozzle piece 302 and the collar 303 and thereby help maintain relative positioning. The brake 361 may include a screw 361A (or other threaded member) and may further include a hole 361B (threaded or otherwise) defined by the collar 303 to receive the screw 361 (or other threaded member). The end of the screw 361A (or other threaded member) may be screwed through the hole 361B and into contact with the oxygen entry-nozzle piece 302 to help prevent or otherwise reduce relative movement between the oxygen entry-nozzle piece 302 and the collar 303.

In at least some embodiments, any of the adjustable ambient air-oxygen blenders disclosed herein may include a brake, which may be the same as and/or similar to the brake 361 or otherwise.

The adjustable ambient air-oxygen blender 300 or any other adjustable ambient air-oxygen blenders disclosed herein may be controlled manually (e.g., by a user) and/or using a machine (e.g., a motor).

The oxygen entry-nozzle piece 302, the collar 303 and/or it exit orifice piece 304 (or one or more portions of the oxygen entry-nozzle piece 302, the collar 303 and/or it exit orifice piece 304) may have cylindrical shape(s) (e.g. as shown), rectangular shape(s) or any other suitable shape(s).

In at least some embodiments, the adjustable ambient air-oxygen blender 300 (or portion(s) thereof) or any other adjustable ambient air-oxygen blender disclosed herein (or portion(s) thereof) may comprise rigid or semi rigid, biocompatible material(s) or any other suitable material(s).

In at least some embodiments, the components of the adjustable ambient air-oxygen blender 300 or any other adjustable ambient air-oxygen blender disclosed herein may be fabricated of thermoplastics, thermoplastic elastomers, elastomers, ceramics, metals, or a combination thereof.

In at least some embodiments, the adjustable ambient air-oxygen blender 300 (or portion(s) thereof) or any other adjustable ambient air-oxygen blender disclosed herein (or portion(s) thereof) may be fabricated by injection molding.

In at least some embodiments, the adjustable ambient air-oxygen blender 300 (or portion(s) thereof) or any other adjustable ambient air-oxygen blender disclosed herein (or portion(s) thereof) may be fabricated of materials compatible for use in a 3D printer.

In at least some embodiments, the adjustable ambient air-oxygen blender 300 (or portion(s) thereof) or any other adjustable ambient air-oxygen blender disclosed herein (or portion(s) thereof) may be fabricated using a 3D printer.

As further described below, in at least some embodiments, the oxygen entry-nozzle piece 302 and the collar 303 may be provided with ribs or other structures (complementary or otherwise) that releasably engage one another. Such structures may assist in securing relative positioning.

Figure 3B:
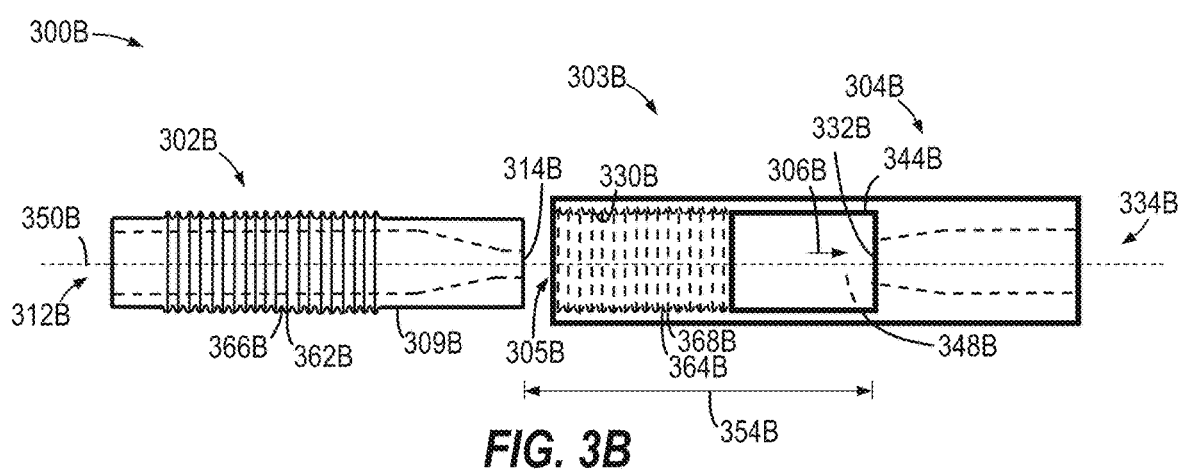
FIG. 3B is a schematic side view of an adjustable ambient air-oxygen blender in a disassembled state, in accordance with at least some embodiments.

FIG. 3B is a schematic side view of an adjustable ambient air-oxygen blender 300B in a disassembled state, in accordance with at least some embodiments.

Referring now to FIG. 3B, in accordance with at least some embodiments, the adjustable ambient air-oxygen blender 300B includes an oxygen entry-nozzle piece 302B, a collar 303B and its exit orifice piece 304B that are similar to the oxygen entry-nozzle piece 302, the collar 303 and its exit orifice piece 304, respectively, of the adjustable ambient air-oxygen blender 300 of FIG. 3A (except where otherwise noted, like reference numerals that differ only in that one is succeeded by the letter "B" are used to indicate like or similar elements) except that the entry-nozzle piece 302B and the collar 303B of the adjustable ambient air-oxygen blender 300B each include a plurality of ribs, e.g., rib 362B and rib 364B, respectively so that the entry-nozzle piece 302B can be inserted into the collar 303B and placed at any of various positions with respect to (e.g., defined by) the ribs, e.g., rib 362B and rib 364B, to releasably secure the relative location of the two pieces 302B, 304B at any of the various positions.

The ability to change a relative positioning of the oxygen entry-nozzle piece 302B and the exit orifice piece 304B provides the ability to change the variable distance 354B between the oxygen exit nozzle 314B and the orifice 332B. The change in the variable distance 354B results in a change to the air-oxygen mixture. The mixture is thus adjustable without any need to stop the flow of oxygen, dismantle a blender from the system, connect a new blender and then resume the flow of oxygen.

The plurality of ribs on the oxygen entry-nozzle piece 302B and the plurality of ribs on the collar 303B, e.g., rib 362B and rib 364B, respectively, may have an annular shape and may be disposed circumferentially about the longitudinal axis 350B (e.g., as shown) or any other suitable shape(s) and/or positioning(s).

The plurality of ribs on the oxygen entry-nozzle piece 302B and the plurality of ribs on the collar 303B, e.g., rib 362B and rib 364B, respectively, may be disposed perpendicular to, substantially perpendicular to or otherwise across (at any suitable angle) the longitudinal axis 350B (e.g., as shown) or in any other suitable orientation(s).

As used herein, the term "substantially perpendicular" means "perpendicular +/−10 degrees, preferably perpendicular +/−5 degrees, more preferably perpendicular +/−1 degree."

The plurality of ribs, e.g., rib 362B, on the oxygen entry-nozzle piece 302B may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 366B, that are offset from one another at least in part in a longitudinal direction and interspersed with the plurality of ribs.

Likewise, the plurality of ribs, e.g., rib 364B, on the collar 303B may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 368B, that are offset from one another at least in part in a longitudinal direction and interspersed with the plurality of ribs.

The plurality of ribs on the oxygen entry-nozzle piece 302B may releasably engage the plurality of ribs on the collar 303B as follows.

With the oxygen entry-nozzle piece 302B and the collar 303B in one of the various relative positions with respect to the ribs, one or more of the plurality of ribs, e.g., rib 362B, of the oxygen entry-nozzle piece 302B may be positioned in one or more of the channels, e.g., channel 368B, defined by the ribs of the collar 303B to thereby create interference to restrict (at least in part) relative movement between the oxygen entry-nozzle piece 302B and the collar 303B (and its exit orifice piece 304B). Likewise, one or more of the plurality of ribs, e.g., rib 364B, of the collar 303B may be positioned in one or more channel, e.g., channel 366B, defined by the ribs of the oxygen entry-nozzle piece 304B to thereby create interference to restrict (at least in part) relative movement between the oxygen entry-nozzle piece 302B and the collar 303B (and its exit orifice piece 304B).

The oxygen entry-nozzle piece 302B and the collar 303B (and its exit orifice piece 304B) may be releasable from a relative positioning by application of suitable force(s) to the oxygen entry-nozzle piece 302B and/or the collar 303B.

In at least some embodiments, the oxygen entry-nozzle piece 302B and collar 303B may have a snug fit and/or a friction fit.

In at least some embodiments, the entry-nozzle piece 302B and the collar 303B may include other structures (complementary or otherwise) that are not ribs but nonetheless have the capability to releasably engage one another and/or releasably secure the oxygen entry-nozzle piece 302B and the collar 303B (and its exit orifice piece 304B) in any of various relative positions with respect to the structures and permit relative movement upon application of suitable force(s) by a user (or otherwise) to the oxygen entry-nozzle piece 302B and/or the collar 303B.

In at least some embodiments, the inner surface 330B of the collar 303B and the outer surface 309B of the oxygen entry-nozzle piece 302B may be provided with screw or other type threads that releasably engage one another to movably couple the oxygen entry-nozzle piece 302B and the exit orifice piece 304B and enable changes to the relative position to be made by rotation of the oxygen entry-nozzle piece 302B and/or the collar 303B (or its exit orifice piece 304B) relative to the other.

Figure 3C:
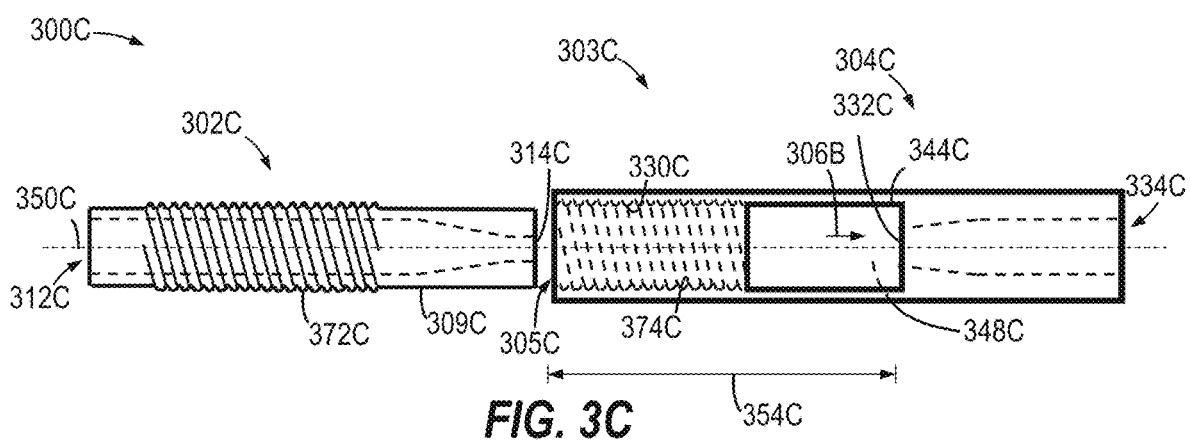
FIG. 3C is a schematic side view of an adjustable ambient air-oxygen blender in a disassembled state, in accordance with at least some embodiments.

FIG. 3C is a schematic side view of an adjustable ambient air-oxygen blender 300C in a disassembled state, in accordance with at least some embodiments.

Referring now to FIG. 3C, in accordance with at least some embodiments, the adjustable ambient air-oxygen blender 300C includes an entry-nozzle piece 302C, a collar 303C and its exit orifice piece 304C that are similar to the oxygen entry-nozzle piece 302B, the collar 303B and its exit orifice piece 304B, respectively, of the adjustable ambient air-oxygen blender 300B of FIG. 3B (except where otherwise noted, like reference numerals that differ only in that one is succeeded by the letter "C" instead of the letter "B" are used to indicate like or similar elements) except that the oxygen entry-nozzle piece 302C and the collar 303C of the adjustable ambient air-oxygen blender 300C each include screw or other type threads, e.g., threads 372C and threads 374C, respectively, that releasably engage one another to movably couple the oxygen entry-nozzle piece 302C and the collar 303C (and its exit orifice piece 304C) and so that the oxygen entry-nozzle piece 302C can be rotated and screwed into the collar piece 303C to change the relative location of the two pieces 302C, 304C.

The threads, e.g., threads 372C and threads 374C, may have a helical shape and may be disposed circumferentially about and/or extend along the longitudinal axis 350C (e.g., as shown) or may have any other suitable shape(s), positioning and/or orientation(s).

The ability to change a relative positioning of the oxygen entry-nozzle piece 302C and the exit orifice piece 304C provides the ability to change the variable distance 354C between the oxygen exit nozzle 314C and the orifice 332C. The change in the variable distance 354C results in a change to the air-oxygen mixture. The mixture is thus adjustable without any need to stop the flow of oxygen, dismantle a blender from the system, connect a new blender and then resume the flow of oxygen.

In at least some embodiments, the oxygen entry-nozzle piece 302C and collar 303C may have a snug fit and/or a friction fit.

As further described below, in at least some embodiments, the collar, e.g., collar 303, 303B and/or 303C, may be part of the oxygen entry-nozzle piece, e.g., oxygen entry-nozzle piece 302, 302B and/or 302C, respectively, and the exit orifice piece, e.g., exit orifice piece 304, 304B and/or 304C, may be separate therefrom.

Figure 3D:
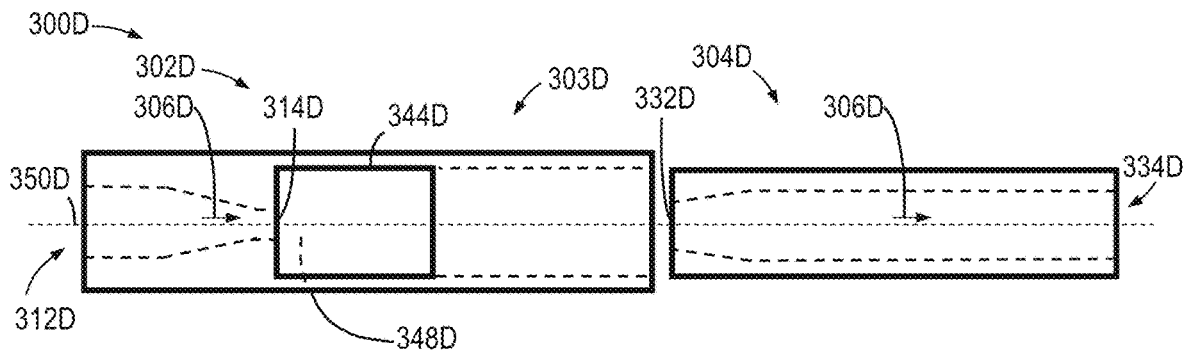
FIG. 3D is a schematic side view of an adjustable ambient air-oxygen blender in a disassembled state, in accordance with at least some embodiments.

FIG. 3D is a schematic side view of an adjustable ambient air-oxygen blender 300D in a disassembled state, in accordance with at least some embodiments.

Referring now to FIG. 3D, in accordance with at least some embodiments, the adjustable ambient air-oxygen blender 300D is similar to the adjustable ambient air-oxygen blender 300 of FIG. 3A (except where otherwise noted, like reference numerals that differ only in that one is succeeded by the letter "D" are used to indicate like or similar elements) except that the entry-nozzle piece 302D includes the collar 303D and the exit orifice piece 304D is separate therefrom. The collar 303D may be configured to slidably or otherwise receive the exit orifice piece 304D in a manner that is the same as or similar to that in which the collar 303 slidably or otherwise receives the oxygen entry-nozzle piece 302 in the adjustable ambient air-oxygen blender 300, to movably couple the oxygen entry-nozzle piece 302D and the exit orifice piece 304D. Thus, the exit orifice piece 304D and the collar 303D may have a snug fit wherein the two pieces 304D, 303D fit snugly and their relative position can be changed, e.g., by sliding the exit orifice piece 304D back and forth, as appropriate to achieve a desired change in relative position between the oxygen entry-nozzle piece 302D and the exit orifice piece 304D.

The snug fit may be a friction fit (a type of interference fit) in which the exit orifice piece 304D and the collar 303D are pressed together and thereafter movably coupled by friction at the interface of the exit orifice piece 304D and the collar 303D. At least some embodiments may employ a friction fit of any desired tightness. As is known, the characteristics of a friction fit depend at least in part on the amount of dimensional interference that is provided at the interface between the two parts.

The ability to change a relative position of the oxygen entry-nozzle piece 302D and the exit orifice piece 304D provides the ability to change a variable distance between the oxygen exit nozzle 314D and the orifice 332D. The change in the variable distance results in a change to the air-oxygen mixture. The mixture is thus adjustable without any need to stop the flow of oxygen, dismantle a blender from the system, connect a new blender and then resume the flow of oxygen.

In the illustrated embodiment, the at least one ambient air entrainment port, e.g., ambient air entrainment port 344D, is defined by the oxygen entry-nozzle piece 302D, which includes the collar 303D.

The ambient air entrainment chamber 348D may be defined at least in part by the oxygen entry-nozzle piece 302D (which includes the collar 303D) and/or the exit orifice piece 304D.

Figure 3E:
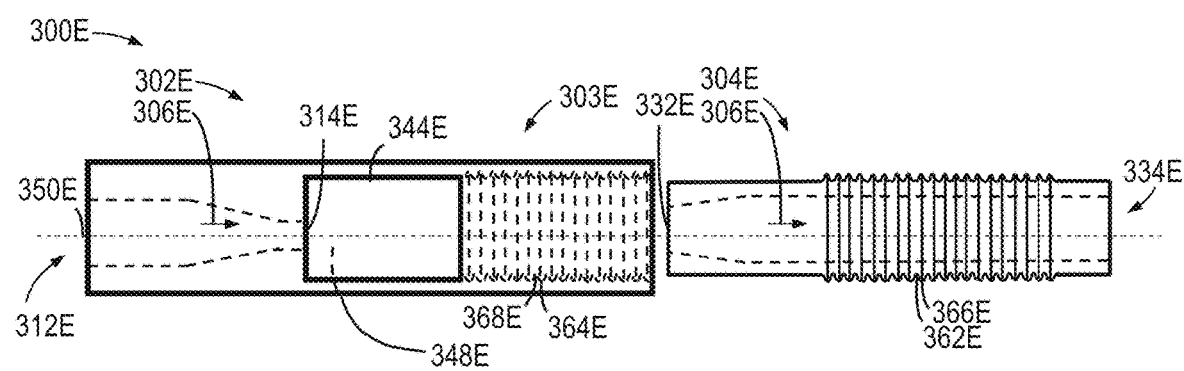
FIG. 3E is a schematic side view of an adjustable ambient air-oxygen blender in a disassembled state, in accordance with at least some embodiments.

FIG. 3E is a schematic side view of an adjustable ambient air-oxygen blender 300E in a disassembled state, in accordance with at least some embodiments.

Referring now to FIG. 3E, in accordance with at least some embodiments, the adjustable ambient air-oxygen blender 300E is similar to the adjustable ambient air-oxygen blender 300B of FIG. 3B (except where otherwise noted, like reference numerals that differ only in that one is succeeded by the letter "E" instead of the letter "B" are used to indicate like or similar elements) except that the entry-nozzle piece 302E includes the collar 303E and the exit orifice piece 304E is separate therefrom. The collar 303E may be configured to slidably or otherwise receive the exit orifice piece 304E in a manner that is the same as or similar to that in which the collar 303B slidably or otherwise receives the oxygen entry-nozzle piece 302B in the adjustable ambient air-oxygen blender 300B, to movably couple the oxygen entry-nozzle piece 302E and the exit orifice piece 304E. Thus, the exit orifice piece 304E and the collar 303E of the oxygen entry-nozzle piece 302E may each include a plurality of ribs, e.g., rib 362E and rib 364E, respectively so that the exit orifice piece 304E can be inserted into the collar 303E and placed at any of various positions with respect to (e.g., defined by) the ribs, e.g., rib 362E and rib 364E, to releasably secure the relative location of the two pieces 304E, 302E at any of the various positions.

The ability to change a relative positioning of the oxygen entry-nozzle piece 302E and the exit orifice piece 304E provides the ability to change a variable distance between the oxygen exit nozzle 314E and the orifice 332E. The change in the variable distance results in a change to the air-oxygen mixture. The mixture is thus adjustable without any need to stop the flow of oxygen, dismantle a blender from the system, connect a new blender and then resume the flow of oxygen.

The plurality of ribs on the exit orifice piece 304E and the plurality of ribs on the collar 303E, e.g., rib 362E and rib 364E, respectively, may have an annular shape and may be disposed circumferentially about the longitudinal axis 350E (e.g., as shown) or any other suitable shape(s) and/or positioning(s).

The plurality of ribs on the exit orifice piece 304E and the plurality of ribs on the collar 303E, e.g., rib 362E and rib 364E, respectively, may be disposed perpendicular to, substantially perpendicular to or otherwise across (at any suitable angle) the longitudinal axis 350E (e.g., as shown) or in any other suitable orientation(s).

The plurality of ribs, e.g., rib 362E, on the exit orifice piece 304E may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 366E, that are offset from one another at least in part in a longitudinal direction and interspersed with the plurality of ribs.

Likewise, the plurality of ribs, e.g., rib 364E, on the collar 303E may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 368E, that are offset from one another at least in part in a longitudinal direction and interspersed with the plurality of ribs.

The plurality of ribs on the exit orifice piece 304E may releasably engage the plurality of ribs on the collar 303E as follows.

With the exit orifice piece 304E and the collar 303E in one of the various relative positions with respect to the ribs, one or more of the plurality of ribs, e.g., rib 362E, of the exit orifice piece 304E may be positioned in one or more of the channels, e.g., channel 368E, defined by the ribs of the collar 303E to thereby create interference to restrict (at least in part) relative movement between the exit orifice piece 304E and the collar 303E. Likewise, one or more of the plurality of ribs, e.g., rib 364E, of the collar 303E may be positioned in one or more channel, e.g., channel 366E, defined by the ribs of the exit orifice piece 304E to thereby create interference to restrict (at least in part) relative movement between the exit orifice piece 304E and collar 303E.

The oxygen entry-nozzle piece 302E and the exit orifice piece 304E may be releasable from a relative positioning by application of suitable force(s) to the oxygen entry-nozzle piece 302B and/or the exit orifice piece 304B.

In at least some embodiments, the oxygen entry-nozzle piece 302E and the exit orifice piece 304E may have a snug fit and/or a friction fit.

In the illustrated embodiment, the at least one ambient air entrainment port, e.g., ambient air entrainment port 344E, is defined by the oxygen entry-nozzle piece 302E, which includes the collar 303E.

The ambient air entrainment chamber 348E may be defined at least in part by the oxygen entry-nozzle piece 302E, which includes the collar 303E, and/or the exit orifice piece 304E.

In at least some embodiments, the entry-nozzle piece 302E and the collar 303E may include other structures (complementary or otherwise) that are not ribs but nonetheless have the capability to releasably engage one another and/or to releasably secure the oxygen entry-nozzle piece 302E and the exit orifice piece 304E in any of various relative positions with respect to the structures and permit relative movement upon application of suitable force(s) by a user (or otherwise) to the oxygen entry-nozzle piece 302E and/or the collar 303E.

In at least some embodiments, the inner surface of the collar 303E and the outer surface of the exit orifice piece 304E may instead be provided with screw or other type threads that releasably engage one another to movably couple the oxygen entry-nozzle piece 302E and the exit orifice piece 304E and enable changes to the relative positioning to be made by rotation of the oxygen entry-nozzle piece 302E and/or the exit orifice piece 304E relative to the other.

Figure 3F:
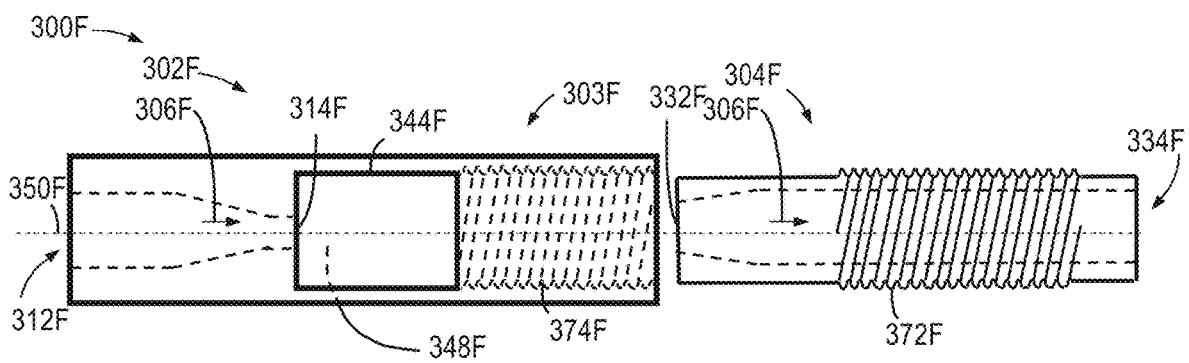
FIG. 3F is a schematic side view of an adjustable ambient air-oxygen blender in a disassembled state, in accordance with at least some embodiments.

FIG. 3F is a schematic side view of an adjustable ambient air-oxygen blender 300F in a disassembled state, in accordance with at least some embodiments.

Referring now to FIG. 3F, in accordance with at least some embodiments, the adjustable ambient air-oxygen blender 300F is similar to the adjustable ambient air-oxygen blender 300C of FIG. 3C (except where otherwise noted, like reference numerals that differ only in that one is succeeded by the letter "F" instead of the letter "C" are used to indicate like or similar elements) except that the entry-nozzle piece 302F includes the collar 303F and the exit orifice piece 304F is separate therefrom. The collar 303F may be configured to slidably or otherwise receive the exit orifice piece 304F in a manner that is the same as or similar to that in which the collar 303C slidably or otherwise receives the oxygen entry-nozzle piece 302C in the adjustable ambient air-oxygen blender 300C, to movably couple the oxygen entry-nozzle piece 302F and the exit orifice piece 304F. Thus, in at least some embodiments, including but not limited to the illustrated embodiment, the exit orifice piece 304F and the collar 303F of the adjustable ambient air-oxygen blender 300F may each include screw or other type threads, e.g., threads 372F and threads 374F, respectively, that releasably engage one another to movably couple the oxygen entry-nozzle piece 302F and the exit orifice piece 304F and so that the exit orifice piece 304F can be rotated and screwed into the collar 303F to change the relative location of the two pieces 304F, 302F.

The threads, e.g., threads 372F and threads 374FC may have a helical shape and may be disposed circumferentially about and/or extend along the longitudinal axis 350F (e.g., as shown) or may have any other suitable shape(s), positioning and/or orientation(s).

In at least some embodiments, the oxygen entry-nozzle piece 302F and the exit orifice piece 304F may have a snug fit and/or a friction fit.

The ability to change a relative positioning of the oxygen entry-nozzle piece 302F and the exit orifice piece 304F provides the ability to change a variable distance between the oxygen exit nozzle 314F and the orifice 332F. The change in the variable distance results in a change to the air-oxygen mixture. The mixture is thus adjustable without any need to stop the flow of oxygen, dismantle a blender from the system, connect a new blender and then resume the flow of oxygen.

In the illustrated embodiment, the at least one ambient air entrainment port, e.g., ambient air entrainment port 344F, is defined by the oxygen entry-nozzle piece 302F, which includes the collar 303F.

The ambient air entrainment chamber 348F may be defined at least in part by the oxygen entry-nozzle piece 302F, which includes the collar 303F, and/or the exit orifice piece 304F.

FIGS. 4A-4J show views of another adjustable ambient air-oxygen blender 400 that includes an oxygen entry nozzle piece 402 and an exit orifice piece 404, in accordance with at least some embodiments.

Figure 4A:
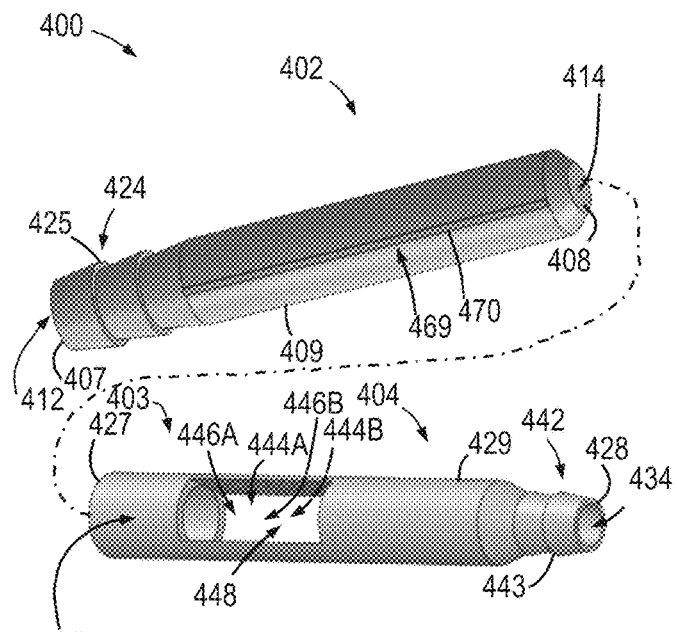
FIG. 4A is a perspective view of an adjustable ambient air-oxygen blender, which includes an oxygen entry-nozzle piece and a collar, in a disassembled state, in accordance with at least some embodiments.

In particular, FIG. 4A is a perspective view showing the adjustable ambient air oxygen blender 400 in a disassembled state, in accordance with at least some embodiments.

Figure 4B:
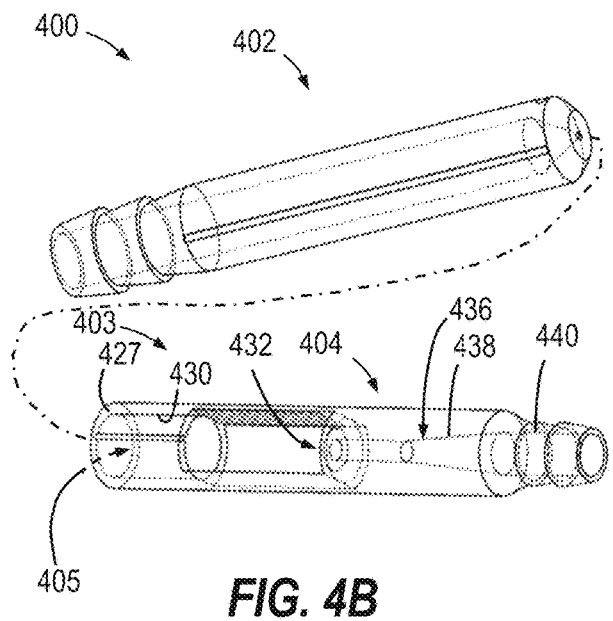
FIG. 4B is a rendering with transparency of a 3-dimensional (3D) computer model of the adjustable ambient air-oxygen blender of FIG. 4A in a disassembled state, in accordance with at least some embodiments.

FIG. 4B is a rendering, with transparency, of a 3-dimensional (3D) computer model of the adjustable ambient air-oxygen blender 400 in a disassembled state, in accordance with at least some embodiments.

Referring now to FIGS. 4A-4B, in accordance with at least some embodiments, the adjustable ambient air-oxygen blender 400 may include a collar 403 that movably couples the oxygen entry-nozzle piece 402 to the exit orifice piece 404. In the illustrated embodiment, the collar 403 includes the exit orifice piece 404 and as discussed below, may define an opening 405 to slidably or otherwise movably receive the oxygen entry-nozzle piece 402 to movably couple the oxygen entry-nozzle piece 402 and the exit orifice piece 404. In some other embodiments, a collar may instead be part of the oxygen entry-nozzle piece 402, and as also discussed below, may define an opening to movably receive the exit orifice piece 404.

Figure 4C:
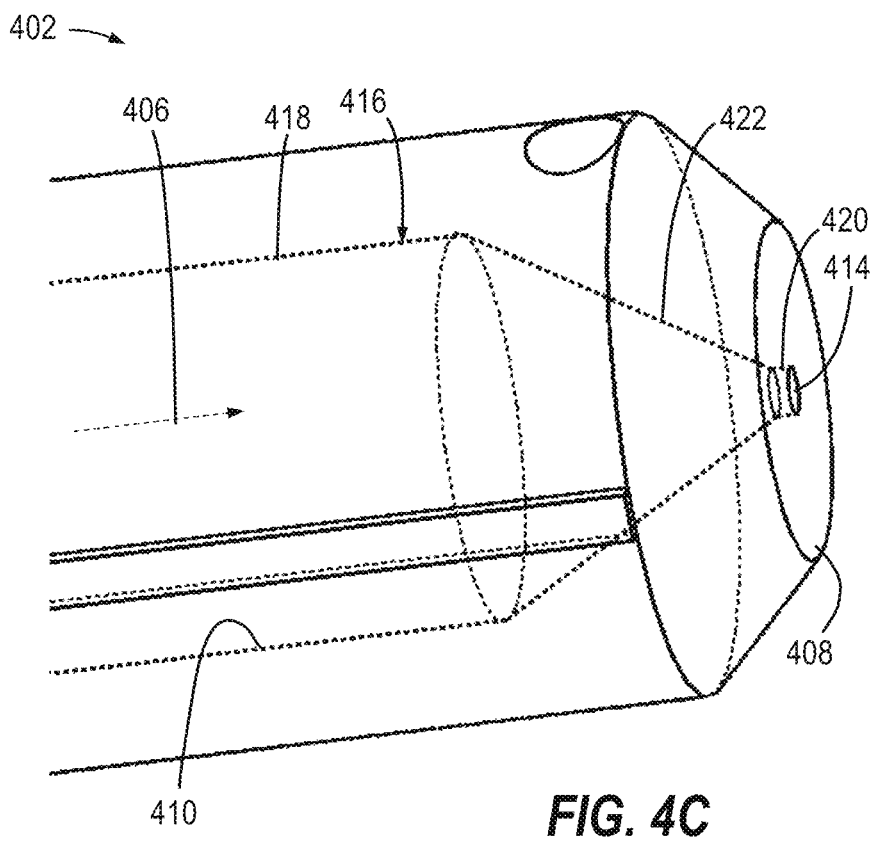
FIG. 4C is an enlarged rendering with transparency of a portion of the 3D computer model of the oxygen entry-nozzle piece of the adjustable ambient air-oxygen blender of FIG. 4A, in accordance with at least some embodiments.

FIG. 4C is an enlarged rendering with transparency of a portion of the 3D computer model of the oxygen entry-nozzle piece 402 of the adjustable ambient air-oxygen blender 400, in accordance with at least some embodiments.

Figure 4D:
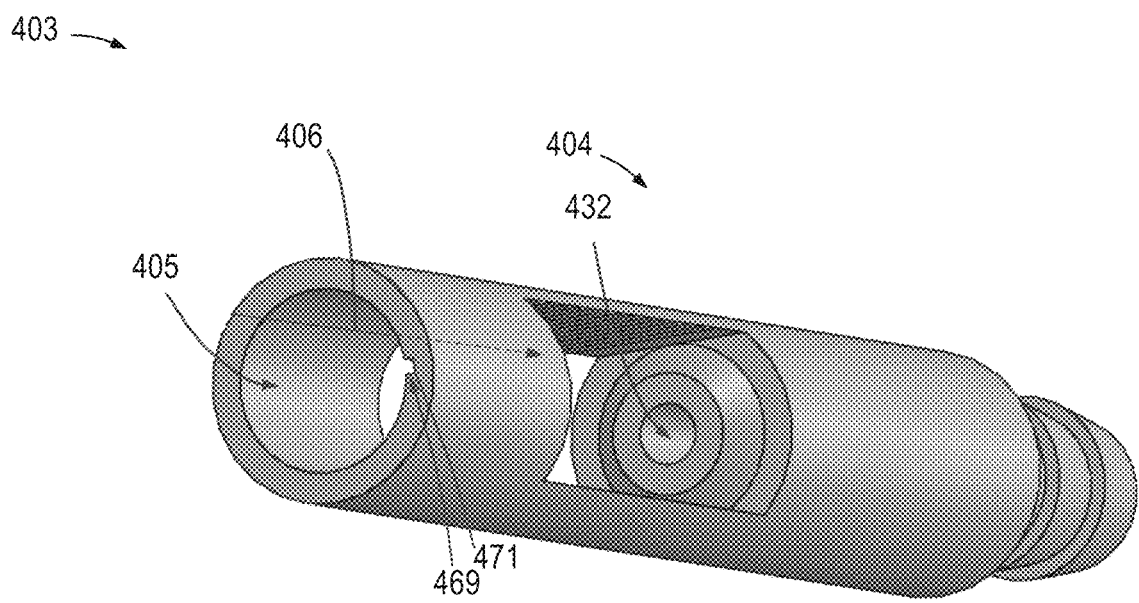
FIG. 4D is a rear perspective view of the collar of the adjustable ambient air-oxygen blender of FIG. 4A, in accordance with at least some embodiments.

FIG. 4D is a rear perspective view of the collar 403 of the adjustable ambient air-oxygen blender 400, in accordance with at least some embodiments.

Figure 4E:
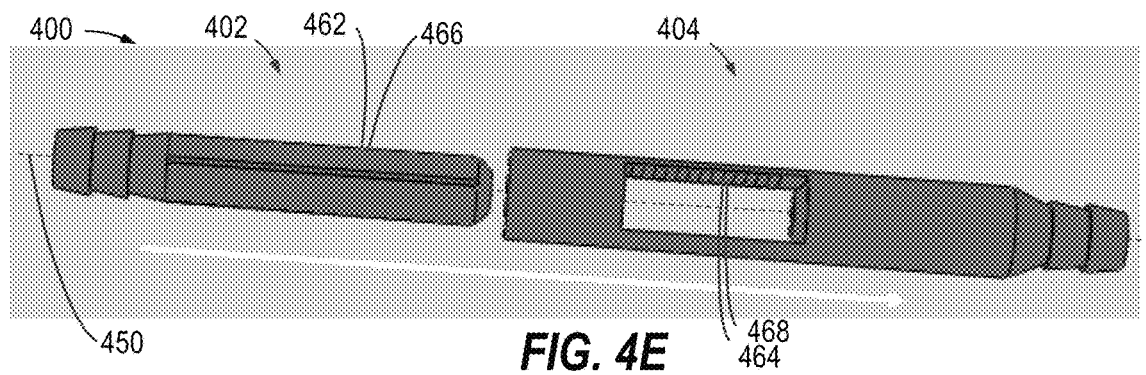
FIG. 4E is a perspective view of the adjustable ambient air-oxygen blender of FIG. 4A in a disassembled state, in accordance with at least some embodiments.

FIG. 4E is a perspective view of the adjustable ambient air-oxygen blender 400 in a disassembled state, in accordance with at least some embodiments.

Referring also now to FIGS. 4C-4E, the adjustable ambient air-oxygen blender 400 defines a gas flow path 406 (FIG. 4C) that extends through the oxygen entry-nozzle piece 402 and the exit orifice piece 404.

The oxygen entry-nozzle piece 402 may have a first end 407, a second end 408, an outer surface 409 and an inner surface 410.

The oxygen entry-nozzle piece 402 defines an inlet 412, a nozzle 414 in fluid communication with the inlet 412, and a channel 416 (FIG. 4C) extending between the inlet 412 and the nozzle 414. The inlet 412 may be disposed at the first end 407 of the oxygen entry-nozzle piece 402 and/or at a first end of the gas flow path 406. The nozzle 414, which may be disposed at the second end 408 of the oxygen entry-nozzle piece 402, is in fluid communication with and downstream of the inlet 412 and may have a cross sectional area that is less than a cross sectional area of the inlet 412. The channel 416 (FIG. 4C) may have one or more spans of uniform cross-sectional diameter, e.g., a span 418 and a span 420, and/or one or more spans of decreasing cross sectional diameter, e.g., a span 422 having a uniformly decreasing or otherwise tapered contour.

The oxygen entry-nozzle piece 402 may include a first connector 424 (FIG. 4A), which may be configured to be releasably or otherwise connected to a tube or other gas line that is coupled (directly and/or indirectly) to an external reservoir (not shown) (and/or other source) of oxygen (or other gas(es)) to be supplied to the adjustable ambient air-oxygen blender 400 and to be mixed with ambient air.

As used herein, the term "gas line" or means a line that has and/or receives gas(es) (of any type(s), e.g., oxygen, a mixture of oxygen and ambient air. It does not require that the line receive only gas(es). The gas line may be said to supply a "supply gas" in this context, which the present invention blends with an "ambient gas" from another place such as the ambient air surrounding the apparatus, or from a second supply source which can substitute for the ambient gas. The mixed gases form a "blended gas" that can be supplied to a patient in some applications.

A gas line may comprise flexible, semi-flexible and/or rigid tubing or any other type of line. A gas line may comprise a connector configured to be connected to a connector (e.g., to be connected to the connector 424 of the oxygen entry-nozzle piece 402).

The first connector 424 may include one or more barbs, e.g., barb 425, which may assist in securing (releasably or otherwise) a tube or other gas line thereto.

The first connector 424 may be disposed at, proximal to and/or otherwise toward the first end 407 of the oxygen entry-nozzle piece 402.

Unless stated otherwise, the term "toward the first end" means closer to the first end than to an opposite end.

The collar 403 and its exit orifice piece 404 may have a first end 427, a second end 428, an outer surface 429 and an inner surface 430. The exit orifice piece 404 defines an orifice 432 (FIG. 4B, 4D), an oxygen-air mixture outlet 434 in fluid communication with the orifice 432, and a channel 436 extending between the orifice 432 and the oxygen-air mixture outlet 434. The orifice 432 is in fluid communication with and downstream of the nozzle 414 and may have a cross sectional area that is greater than the cross-sectional area of the nozzle 414. The oxygen-air mixture outlet 434, which may be disposed at a second end of the gas flow path 406, is downstream of the orifice 432 and may have a cross sectional area that is greater than the cross-sectional area of the orifice 432. The channel 436 may have one or more spans of increasing cross sectional diameter, e.g., a span 438 having a uniformly increasing or otherwise tapered contour, and/or one or more spans of uniform cross-sectional diameter, e.g., a span 440.

The collar 403 may include a second connector 442, which may be configured to be releasably or otherwise connected to a tube or other gas line that is coupled (directly and/or indirectly) to a nasal or other breathing apparatus and/or other destination to which a mixture from the adjustable ambient air-oxygen blender 400 is to be supplied.

The second connector 442 may be disposed at, proximal to and/or otherwise toward the second end 428 of the collar 403.

Unless stated otherwise, the term "toward the second end" means closer to the second end than to an opposite end.

The second connector 442 may include one or more barbs, e.g., barb 443, which may assist in securing (releasably or otherwise) a tube or other gas line thereto.

In at least some embodiments, any of the adjustable ambient air-oxygen blenders disclosed herein may include one or more connector, which may be the same as and/or similar to one or more of the connectors 424, 442 or otherwise.

The adjustable ambient air-oxygen blender 400 defines at least one ambient air entrainment port, e.g., ambient air entrainment ports 444A (in FIG. 4A, defined by the near side of the adjustable ambient air-oxygen blender 400), 444B (in FIG. 4A, defined by the far side of the adjustable ambient air-oxygen blender 400), that provides at least one flow path, e.g., flow paths 446A (in FIG. 4A, through the near side of the adjustable ambient air-oxygen blender 400), 446B (in FIG. 4A, through the far side of the adjustable ambient air-oxygen blender 400), for ambient air to enter the adjustable ambient air-oxygen blender 400. In at least some embodiments, the at least one ambient air entrainment port, e.g., ambient air entrainment ports 444A, 444B, is defined at least in part by the oxygen entry-nozzle piece 402 and/or the collar 403. In the illustrated embodiment, the at least one ambient air entrainment port, e.g., ambient air entrainment ports 444A, 444B, is defined by the collar 403. The at least one ambient air entrainment port, e.g., ambient air entrainment ports 444A, 444B, may have a rectangular cross section (e.g., as shown) or any other suitable configuration.

The adjustable ambient air-oxygen blender 400 may further define an ambient air entrainment chamber 448 in fluid communication with the nozzle 414 to receive oxygen that exits therefrom and in fluid communication with the at least one ambient air entrainment port, e.g., ambient air entrainment ports 444A, 444B, to receive ambient air that enters the adjustable ambient air-oxygen blender 400 therethrough. In at least some embodiments, including but not limited to the illustrated embodiment, the ambient air entrainment chamber 448 is disposed (at least in part) between the nozzle 414 and the orifice 432 and/or in fluid communication between the nozzle 414 and the orifice 432. In at least some embodiments, including but not limited to the illustrated embodiment, the ambient air entrainment chamber 448 is defined at least in part by the oxygen entry-nozzle piece 402 and/or the collar 403.

The adjustable ambient air-oxygen blender 400 may have a longitudinal axis 450 (FIG. 4E), which may extend in a longitudinal direction. The oxygen entry-nozzle piece 402, the collar 403 and/or its exit orifice piece 404 may be disposed along and/or about the longitudinal axis 450 and/or may have a longitudinal axis coincident (or substantially coincident) with the longitudinal axis 450.

The flow path 406 (or one or more portions thereof) may be disposed along and/or about the longitudinal axis 450 and/or may have a longitudinal axis coincident (or substantially coincident) with the longitudinal axis 450.

As stated above, the collar 403 may define an opening 405 to slidably or otherwise movably receive the oxygen entry-nozzle piece 402 to movably couple the oxygen entry-nozzle piece 402 and the exit orifice piece 404.

In at least some embodiments, the entry-nozzle piece 402 and the collar 403 may each include a plurality of ribs, e.g., rib 462 (FIG. 4E) and rib 464 (FIG. 4E), respectively, so that the entry-nozzle piece 402 can be inserted into the collar 403 and placed at any of various positions with respect to (e.g., defined by) the ribs, e.g., rib 462 and rib 464, to releasably secure the relative location of the two pieces 402, 403) at any of the various positions.

Figure 4F:
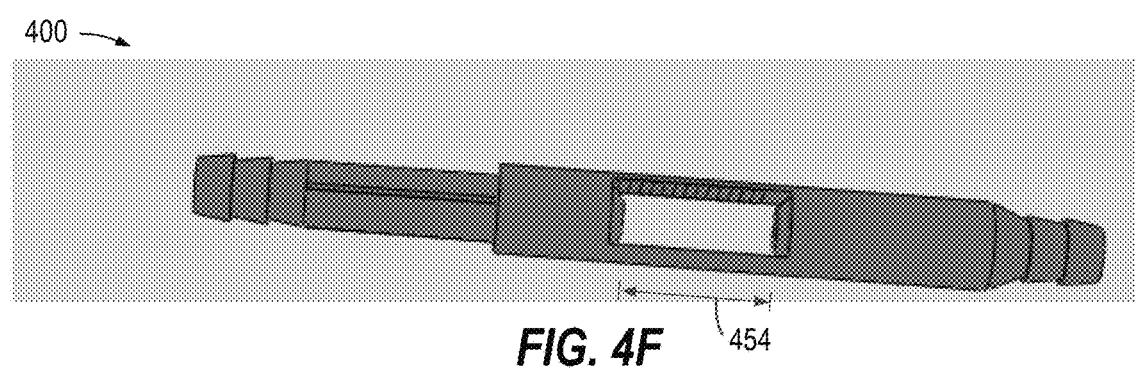
FIG. 4F is a perspective view of the adjustable ambient air-oxygen blender of FIG. 4A in an assembled state, with the oxygen entry-nozzle piece and the collar in a first relative positioning, in accordance with at least some embodiments.
Figure 4G:
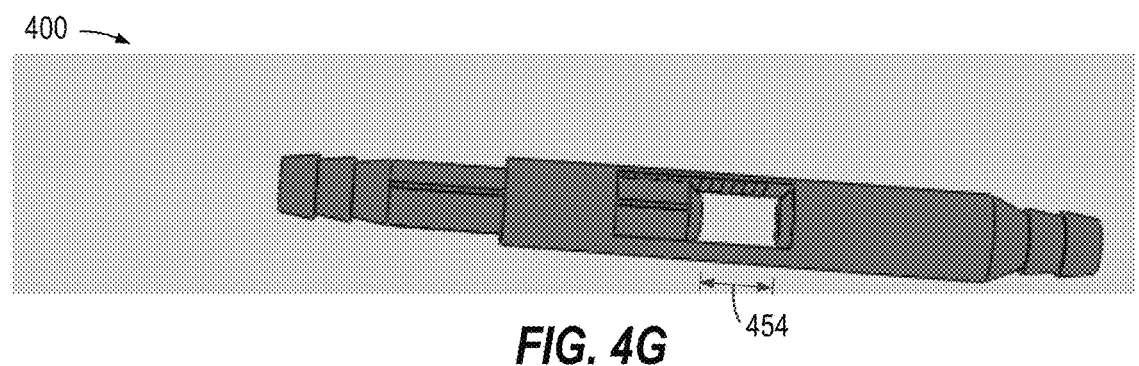
FIG. 4G is a perspective view of the adjustable ambient air-oxygen blender of FIG. 4A in an assembled state, with the oxygen entry-nozzle piece and the collar in a second relative positioning, in accordance with at least some embodiments.
Figure 4H:
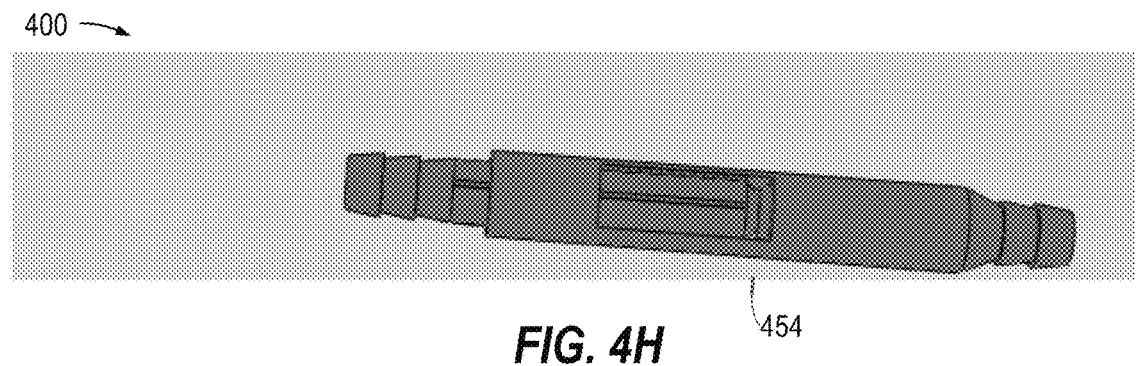
FIG. 4H is a perspective view of the adjustable ambient air-oxygen blender of FIG. 4A in an assembled state, with the oxygen entry-nozzle piece and the collar in a third relative positioning, in accordance with at least some embodiments.

FIGS. 4F-4H show views of the adjustable ambient air-oxygen blender 400 as an assembly of the two pieces so that the nozzle 414 and orifice 432 are at various distances from each other. The change in distance between the nozzle 414 and the orifice 432 results in a change to the air-oxygen mixture. The mixture is thus adjustable without any need to stop the flow of oxygen, dismantle a blender from the system, connect a new blender and then resume the flow of oxygen.

In particular, FIG. 4F is a perspective view of the adjustable ambient air-oxygen blender 400 in an assembled state, with the oxygen entry-nozzle piece 402 and the collar 403 in a first relative positioning, in accordance with at least some embodiments.

FIG. 4G is a perspective view of the adjustable ambient air-oxygen blender 400 in an assembled state, with the oxygen entry-nozzle piece 402 and the collar 403 in a second relative positioning, in accordance with at least some embodiments.

FIG. 4H is a perspective view of the adjustable ambient air-oxygen blender 400 in an assembled state, with the oxygen entry-nozzle piece 402 and the collar 403 in a third relative positioning, in accordance with at least some embodiments.

Figure 4I:
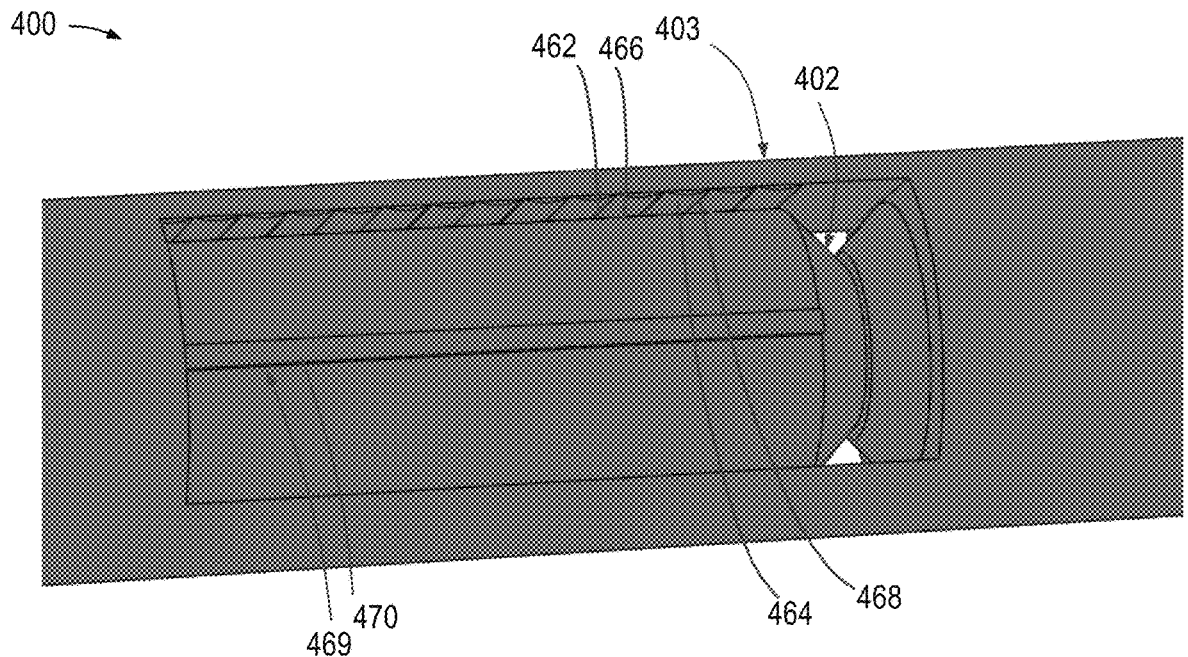
FIG. 4I is an enlarged perspective view of a portion of the adjustable ambient air-oxygen blender of FIG. 4A in an assembled state, with the oxygen entry-nozzle piece and the collar in the third relative positioning, in accordance with at least some embodiments.

FIG. 4I is an enlarged perspective view of a portion of the adjustable ambient air-oxygen blender 400 in an assembled state, with the oxygen entry-nozzle piece 402 and the collar 403 in the third relative positioning, in accordance with at least some embodiments.

Figure 4J:
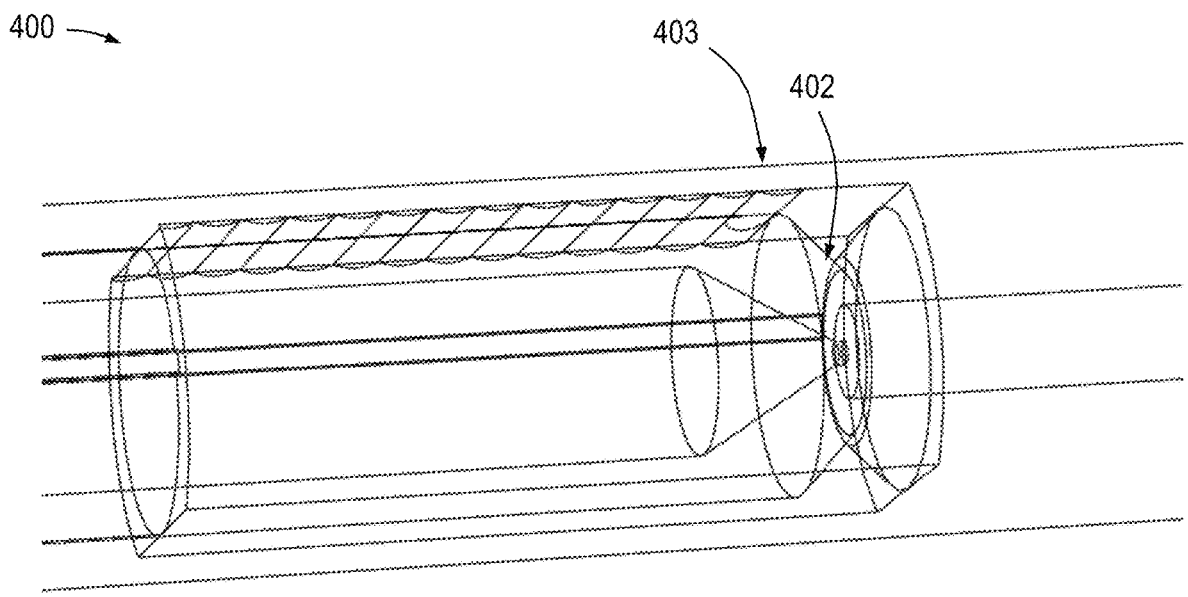
FIG. 4J is an enlarged rendering with transparency of a portion of the 3D computer model of the adjustable ambient air-oxygen blender of FIG. 4A in an assembled state, with the oxygen entry-nozzle piece and the collar in the third relative positioning, in accordance with at least some embodiments.

FIG. 4J is an enlarged rendering with transparency of a portion of the 3D computer model of the adjustable ambient air-oxygen blender 400 in an assembled state, with the oxygen entry-nozzle piece 402 and the collar 403 in the third relative positioning, in accordance with at least some embodiments.

Referring also now to FIGS. 4F-4H, with the oxygen entry-nozzle piece 402 and the collar 403 in the first relative positioning, the adjustable ambient air-oxygen blender 400 has a first distance 454 (FIG. 4F) between the nozzle 414 and the orifice 432, and a first percentage of oxygen in the mixture.

In the second relative positioning, the adjustable ambient air-oxygen blender 400 has a second distance 454 (FIG. 4G) between the nozzle 414 and the orifice 432, and a second percentage of oxygen in the mixture.

The second distance 454 (FIG. 4G) is less than the first distance 454 (FIG. 4F). This has the effect of increasing the percentage of oxygen in the mixture. The second percentage of oxygen in the mixture is thus greater than the first percentage of oxygen in the mixture.

In at least some embodiments, the change in the relative position that results in the change in the variable distance 454 may result in a portion of the oxygen entry-nozzle piece 402 being disposed in line with at least a portion of the at least one air-entrainment port, e.g., the air entrainment ports 444A, 444B. This may reduce the amount of ambient air that enters the adjustable ambient air-oxygen blender 400 to mix into the flowing oxygen, which has the effect of further increasing the percentage of oxygen in the air oxygen mixture.

In the third relative positioning, the adjustable ambient air-oxygen blender 400 has a third distance 454 (FIG. 4H) between the nozzle 414 and the orifice 432, and a third percentage of oxygen in the mixture.

The third distance 454 (FIG. 4H) is less than the second distance 454 (FIG. 4G). This has the effect of increasing the percentage of oxygen in the mixture.

Moreover, in the third positioning, ambient air is blocked or at least nearly blocked from mixing into the flowing oxygen, which has the effect of further increasing the percentage of oxygen in the air oxygen mixture.

The third percentage of oxygen in the mixture is thus greater than the second percentage of oxygen in the mixture and greater than the first percentage of oxygen in the mixture.

The mixture is thus adjustable without any need to stop the flow of oxygen, dismantle a blender from the system, connect a new blender and then resume the flow of oxygen.

The plurality of ribs on the oxygen entry-nozzle piece 402, e.g., rib 462, may extend at least in part across the oxygen entry-nozzle piece 402 (e.g., as shown). Likewise, the plurality of ribs on the collar 403, e.g., rib 464, may extend at least in part across the collar 403 (e.g., as shown).

The plurality of ribs on the oxygen entry-nozzle piece 402, e.g., rib 462 (FIG. 4E), and the plurality of ribs on the collar 403, e.g., rib 464 (FIG. 4E), may be disposed perpendicular to (or at least substantially perpendicular to) (e.g., as shown) or otherwise across (at any suitable angle) the longitudinal axis 450 or in any other suitable orientation(s). In at least some embodiments, the ribs may be straight (e.g., as shown) or may have any other suitable size(s), shape(s) and/or positioning(s).

The plurality of ribs, e.g., rib 462 (FIG. 4E), on the oxygen entry-nozzle piece 402 may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 466 (FIG. 4E), that are offset from one another at least in part in a longitudinal direction and interspersed with the plurality of ribs.

Likewise, the plurality of ribs, e.g., rib 464 (FIG. 4E), on the collar 403 may be arranged in a rib array that extends at least in part in a longitudinal direction, with successive ribs in the rib array being offset from one another at least in part in the longitudinal direction. Successive ribs in the rib array may define a channel therebetween. The rib array as a whole may thus define a plurality of channels, e.g., channel 468 (FIG. 4E), that are offset from one another at least in part in a longitudinal direction and interspersed with the plurality of ribs.

The plurality of ribs on the oxygen entry-nozzle piece 402 may releasably engage the plurality of ribs on the collar 403 as follows.

With the oxygen entry-nozzle piece 402 and the collar 403 in one of the various relative positions with respect to (e.g., defined by) the ribs, one or more of the plurality of ribs, e.g., rib 462 (FIG. 4E), of the oxygen entry-nozzle piece 402 may be positioned in one or more of the channels, e.g., channel 468 (FIG. 4E), defined by the ribs of the collar 403 to thereby create interference to restrict (at least in part) relative movement between the oxygen entry-nozzle piece 402 and the collar 403 (and its exit orifice piece 404). Likewise, one or more of the plurality of ribs, e.g., rib 464 (FIG. 4E), of the collar 403 may be positioned in one or more channel, e.g., channel 466 (FIG. 4E), defined by the ribs of the oxygen entry-nozzle piece 402 to thereby create interference to restrict (at least in part) relative movement between the oxygen entry-nozzle piece 402 and the collar 403 (and its exit orifice piece 404).

The oxygen entry-nozzle piece 402 and the exit orifice piece 404 may be releasable from a relative positioning by application of suitable force(s) to the oxygen entry-nozzle piece 402 and/or the collar 403.

The oxygen entry-nozzle piece 402 and the collar 403 may collectively define one or more guide, e.g., guide 469 (FIGS. 4A, 4I), to ensure a desired angular orientation between the oxygen entry-nozzle piece 402 and the collar 403 during and/or after assembly of the adjustable ambient air-oxygen blender 400. In at least some embodiments, including but not limited to the illustrated embodiment, the one or more guide, e.g., guide 469, ensures that the plurality of ribs on the oxygen entry-nozzle piece 402 will be sufficiently aligned with the plurality of ribs on the collar 403 so as to engage therewith at least upon completion of assembly of the adjustable ambient air-oxygen blender 400.

The one or more guide, e.g., guide 469, may comprise a first structure 470 (FIGS. 4A, 4I) defined by the oxygen entry-nozzle piece 402 and a second structure 471 (FIG. 4D) (complementary or otherwise to the first structure 470) that is defined by the collar 403 and engages with the first structure 470 at least upon completion of assembly of the adjustable ambient air-oxygen blender 400.

In at least some embodiments, the first structure 470 comprises a rail or other raised portion and the second structure 471 comprises a channel or other recessed portion (e.g., as shown) that receives the rail or other raised portion.

In at least some other embodiments, the first structure 470 comprises a channel or other recessed portion and the second structure 471 comprises a rail or other raised portion.

The channel or other recessed portion and the rail or other raised portion may each extend in a longitudinal direction and/or parallel (or at least substantially parallel) to the longitudinal axis 450 (e.g., as shown) or may have any other suitable shape(s) and/or orientation(s). The rail or other raised portion may or may not be continuous and/or uniform and may or may not have a same length as the channel. In at least some embodiments, the rail or other raised portion may comprise a stub or a plurality of stubs (of same or different lengths).

In at least some embodiments, any of the adjustable ambient air-oxygen blenders disclosed herein may include one or more guide, which may be the same as and/or similar to the one or more guide, e.g., guide 469, or otherwise.

In at least some other embodiments, the plurality of ribs on the oxygen entry-nozzle piece 402, e.g., rib 462, and the plurality of ribs on the collar 403, e.g., rib 464, may instead have an annular shape and may be disposed circumferentially about the longitudinal axis 450 or any other suitable shape(s) and/or positioning(s), e.g., as described above with respect to the adjustable ambient air-oxygen blender 300B (FIG. 3B).

The oxygen entry-nozzle piece 402, the collar 403 and/or it exit orifice piece 404 (or one or more portions of the oxygen entry-nozzle piece 402, the collar 403 and/or it exit orifice piece 404) may have cylindrical shape(s) (e.g. as shown), rectangular shape(s) or any other suitable shape(s).

Figure 4K:
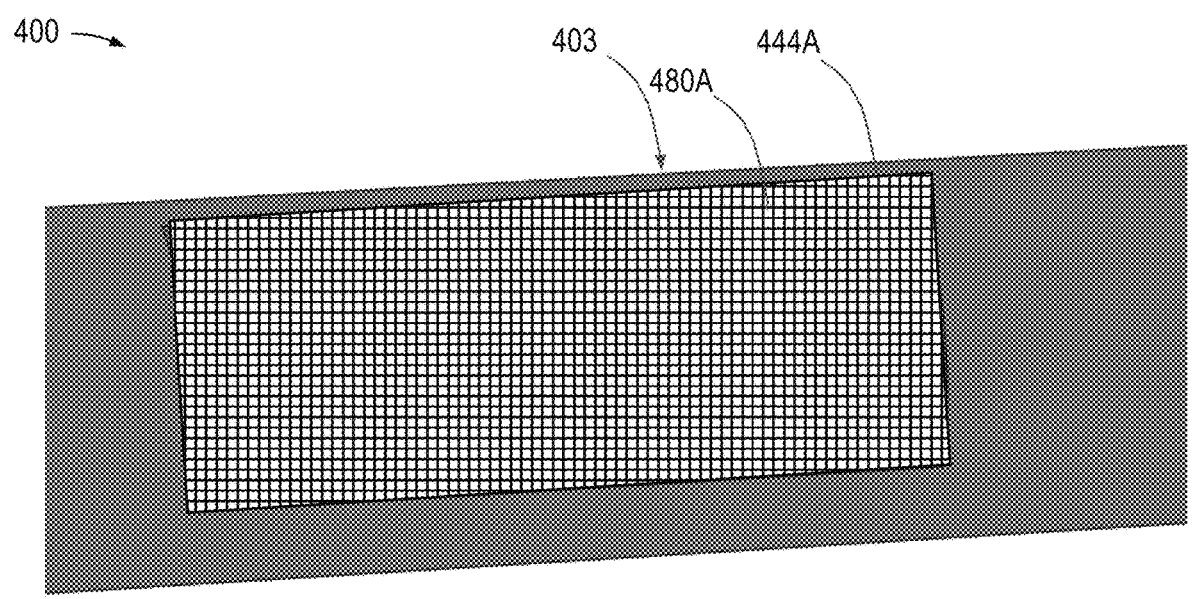
FIG. 4K is an enlarged perspective view of the collar of the adjustable ambient air-oxygen blender of FIG. 4A and an optional filter, in accordance with at least some embodiments.

FIG. 4K is an enlarged perspective view of the collar of the adjustable ambient air-oxygen blender 400 and an optional filter 480A, in accordance with at least some embodiments.

Referring also now to FIG. 4K, in at least some embodiments, the adjustable ambient air-oxygen blender 400 may include at least one ambient air filter, e.g., ambient air filter 480A, that filters at least in part (particles and/or chemicals) that pass through the filter. In at least some embodiments, each air filter of the at least one ambient air filter, e.g., ambient air filter 480A, may be disposed to cover or otherwise in register at least in part with a respective one of the at least one ambient air entrainment port, e.g., ambient air entrainment port 444A, so as to filter at least in part ambient air that enters or is to enter the adjustable ambient air-oxygen blender 400 through the respective one of the at least one ambient air entrainment port, e.g., ambient air entrainment port 444A. Each air filter of the at least one ambient air filter, e.g., ambient air filter 480A, may have a size and/or shape that is the same as and/or similar to the size and/or shape of the respective one of the at least one ambient air entrainment port, e.g., ambient air entrainment port 444A, and/or any other suitable size(s), shape(s) and/or positioning(s).

In at least some embodiments, any of the adjustable ambient air-oxygen blenders disclosed herein, may include at least one ambient air filter, which may be the same as and/or similar to the at least one ambient air filter, e.g., ambient air filter 480A, or otherwise.

In at least some embodiments, one or more air filters may alternatively or additionally be provided in one or more other locations downstream of any of the adjustable ambient air-oxygen blenders disclosed herein.

In at least some embodiments, the entry-nozzle piece 402 and the collar 403 may include other structures (complementary or otherwise) that are not ribs but nonetheless have the capability to releasably engage one another and/or to releasably secure the oxygen entry-nozzle piece 402 and the exit orifice piece 404 in any of various relative positions with respect to the structures and permit relative movement upon application of suitable force(s) by a user (or otherwise) to the oxygen entry-nozzle piece 402 and/or the collar 403.

In at least some embodiments, the oxygen entry-nozzle piece 402 and collar 403 may have a snug fit and/or a friction fit.

In at least some embodiments, the oxygen entry-nozzle piece 402 and collar 403 may not include ribs but may have a snug fit and/or friction fit, e.g., as described above with respect to the adjustable ambient air-oxygen blender 300 (FIG. 3A).

In at least some embodiments, instead of ribs, the oxygen entry-nozzle piece 402 and the collar 403 may each include screw or other type threads, e.g., threads that are the same as or similar to threads 372C and threads 374C described above with respect to the adjustable ambient air-oxygen blender 300C (FIG. 3C), that releasably engage one another to movably couple the oxygen entry-nozzle piece 402 and the exit orifice piece 404 and so that the oxygen entry-nozzle piece 402 can be rotated and screwed into the collar piece 403 to change the relative location of the two pieces 402, 404, e.g., as in the adjustable ambient air-oxygen blender 300C (FIG. 3C).

In at least some embodiments, the collar 403 may be part of the oxygen entry-nozzle piece 402 and the exit orifice piece may be separate therefrom, e.g., as in the adjustable ambient air-oxygen blender 300D (FIG. 3D), the adjustable ambient air-oxygen blender 300E (FIG. 3E) and/or the adjustable ambient air-oxygen blender 300F (FIG. 3F).

In at least some of such embodiments, the at least one ambient air entrainment port, e.g., ambient air entrainment ports 444A, 444B, may be defined by the oxygen entry-nozzle piece 402 that includes the collar 403, e.g., as described above with respect to the adjustable ambient air-oxygen blender 300D (FIG. 3D), the adjustable ambient air-oxygen blender 300E (FIG. 3E) and/or the adjustable ambient air-oxygen blender 300F (FIG. 3F).

In at least some of such embodiments, the ambient air entrainment chamber 448 may be defined at least in part by the oxygen entry-nozzle piece 402 and/or the exit orifice piece 404, e.g., as described above with respect to the adjustable ambient air-oxygen blender 300D (FIG. 3D), the adjustable ambient air-oxygen blender 300E (FIG. 3E) and/or the adjustable ambient air-oxygen blender 300F (FIG. 3F).

As further described below, in at least some embodiments, the distance between a nozzle and an orifice in an adjustable ambient air-oxygen blender may be fixed.

In other words, the apparatus in some embodiments comprises two body parts, or sleeves, which can fit inside one another. An inner sleeve slidably moveable within the outer sleeve. The sleeves may be hollow and define an axis running through them, and the supply (e.g., oxygen) gas may flow through the apparatus substantially along said axis from an inlet port to an outlet port. Along the way an ambient air window defined in the outer sleeve is variably occluded by the inner sleeve, depending on its position, so as to vary the amount of ambient gas being entrained into the blender apparatus.

FIG. 5A is a schematic side view of an adjustable ambient air-oxygen blender 500 that includes a fixed blender 501 (and a collar 503 that movably couples to the fixed blender 501, shown in a disassembled state, in accordance with at least some embodiments.

FIG. 5D is a schematic end view of the fixed blender 501 and the collar 503 of the adjustable ambient air-oxygen blender 500, in accordance with at least some embodiments.

Referring now to FIGS. 5A and 5D, in accordance with at least some embodiments, the collar 503 may define an opening 505 to movably receive the fixed blender 501 to movably couple the fixed blender 501 and the collar 503. In at least some embodiments, the fixed blender 501 and the collar 503 are rotatably coupled.

The adjustable ambient air-oxygen blender 500 defines a gas flow path 506 that extends through the fixed air blender 501.

The fixed blender 501 may have a first end 507, a second end 508, an outer surface 509 and an inner surface 510.

The fixed blender 501 defines an inlet 512, a nozzle 514 in fluid communication with the inlet 512, a channel 516 extending between the inlet 512 and the nozzle 514, an orifice 532, an oxygen-air mixture outlet 534 in fluid communication with the orifice 532, and a channel 536 extending between the orifice 532 and the oxygen-air mixture outlet 534. The inlet 512 may be disposed at the first end 507 of the fixed blender 501 and/or at a first end of the gas flow path 506. The nozzle 514 is in fluid communication with and downstream of the inlet 512 and may have a cross sectional area that is less than a cross sectional area of the inlet 512. The channel 516 may have one or more spans of uniform cross-sectional diameter, e.g., a span 518 and a span 520, and/or one or more spans of decreasing cross sectional diameter, e.g., a span 522 having a uniformly decreasing or otherwise tapered contour. The orifice 532 is in fluid communication with and downstream of the nozzle 514 and may have a cross sectional area that is greater than the cross-sectional area of the nozzle 514. The oxygen-air mixture outlet 534, which may be disposed at a second end of the gas flow path 506, is downstream of the orifice 532 and may have a cross sectional area that is greater than the cross-sectional area of the orifice 532. The channel 536 may have one or more spans of increasing cross sectional diameter, e.g., a span 538 having a uniformly increasing or otherwise tapered contour, and/or one or more spans of uniform cross-sectional diameter, e.g., a span 540.

The fixed blender 501 further defines at least one ambient air entrainment port, e.g., ambient air entrainment port 544, that provides a flow path, e.g., flow path 546, for ambient air to enter the adjustable ambient air-oxygen blender 500. The at least one ambient air entrainment port, e.g., ambient air entrainment port 544, may have a rectangular cross section (e.g., as shown) or any other suitable configuration.

The fixed blender 501 may further define an ambient air entrainment chamber 548 in fluid communication with the nozzle 514 to receive oxygen that exits therefrom and in fluid communication with the at least one ambient air entrainment port, e.g., ambient air entrainment port 544, to receive ambient air that enters the adjustable ambient air-oxygen blender 500 therethrough. In at least some embodiments, including but not limited to the illustrated embodiment, the ambient air entrainment chamber 548 is disposed (at least in part) between the nozzle 514 and the orifice 532 and/or in fluid communication between the nozzle 514 and the orifice 532.

The adjustable ambient air-oxygen blender 500 may have a longitudinal axis 550, which may extend in a longitudinal direction. The fixed blender 501 and/or collar 503 may be disposed along and/or about the longitudinal axis 550 and/or may have a longitudinal axis coincident (or substantially coincident) with the longitudinal axis 550.

The flow path 506 (or one or more portions thereof) may be disposed along and/or about the longitudinal axis 550 and/or may have a longitudinal axis coincident (or substantially coincident) with the longitudinal axis 550.

The fixed blender 501 may further include an o-ring 551, further discussed below, and/or a stop 552.

In at least some embodiments, the stop 552 limits travel by the collar 503 in a longitudinal direction, e.g. in a direction toward the second end 508 of the fixed blender 501.

In at least some embodiments, any of the adjustable ambient air-oxygen blenders disclosed herein may include one or more stops, which may be the same as and/or similar to the stop, e.g., stop 552, or otherwise.

The collar 503 may have a first end 527, a second end 528, an outer surface 529 and an inner surface 530.

As stated above, the collar 503 may define an opening 505 to slidably or otherwise receive the fixed blender 501 to movably couple the fixed blender 501 and the collar 503. In at least some embodiments, the fixed blender 501 and the collar 503 are rotatably coupled.

The collar 503 may further define at least one opening, e.g., opening 553, which may be longitudinally aligned (at least in part) with the at least one ambient air entrainment port, e.g., the ambient air entrainment port 544, to provide at least one flow path through which ambient air may flow to reach the at least one ambient air entrainment port, e.g., the ambient air entrainment port 544, if the at least one opening, e.g., opening 553, and the at least one ambient air entrainment port, e.g., the ambient air entrainment port 544, are radially aligned (at least in part). The at least one opening, e.g., opening 553, may have a rectangular cross section (e.g., as shown) or any other suitable configuration.

In at least some embodiments, including but not limited to the illustrated embodiment, the collar 503 slides over the first end 507 of the fixed blender 501 and fits snugly to it to releasably secure the collar 503 to the fixed blender 501 and so that the collar 503 can be rotated (upon application of suitable force(s) by a user (or otherwise) to the fixed blender 501 and/or the collar 503) to different angular positions relative to the fixed blender 501 to cover different areas of the one or more air-entrainment ports, e.g., air-entrainment port 544, of the fixed blender 501 to limit to different extents the amount of ambient air that enters the fixed blender 501 to mix into the flowing oxygen.

Thus, the fixed blender 501 and/or collar 503 may be rotated relative to the other to cause the collar 503 to cover a variable size extent of the at least one ambient air entrainment port, e.g., ambient air entrainment port 544, and thereby limit to a variable extent the amount of ambient air that enters the adjustable ambient air-oxygen blender 500 through the at least one ambient air entrainment port, e.g., ambient air entrainment port 544.

The above ability to control the amount of ambient air that enters the fixed blender 501 to mix into the flowing oxygen provides the ability to change the air-oxygen mixture. The mixture is thus adjustable without any need to stop the flow of oxygen, dismantle a blender from the system, connect a new blender and then resume the flow of oxygen.

The snug fit may be a friction fit (a type of interference fit) in which the fixed blender 501 and collar 503 are pressed together and thereafter movably coupled by friction at an interface of the collar 503 and the fixed blender 501.

In at least some embodiments, the snug fit results from an interface between the o-ring 551 of the fixed blender 501 and the inner surface 530 of the collar 503.

The o-ring 551 may comprise a polymer (e.g., rubber and/or plastic) and/or any other suitable material(s).

At least some embodiments may employ a friction fit of any desired tightness. As is known, the characteristics of a friction fit depend at least in part on the amount of dimensional interference that is provided at the interface between the two parts. In at least some embodiments, a friction fit of any suitable tightness may be provided by an interface between the o-ring 551 or other part of the fixed blender 501 and the inner surface 530 of the collar 503.

In at least some embodiments, a snug fit and/or a friction fit provides resistance to relative movement (longitudinal and/or rotational) between the collar 503 and fixed blender 501 to thereby movably couple and/or releasably secure the collar 503 to the fixed blender 501.

The fixed blender 501 and/or the collar 503 (or one or more portions of the fixed blender 501 and/or the collar 503) may have cylindrical shape(s) (e.g. as shown), rectangular shape(s) or any other suitable shape(s).

As further described below, in at least some embodiments, the fixed blender 501 and the collar 503 are provided with ribs or other structures (complementary or otherwise) that releasably engage one another.

FIG. 5B is a schematic side view of an adjustable ambient air-oxygen blender 500B that includes a fixed blender 501B and a collar 503B that slides over the fixed blender 501B and movably couples to the fixed blender 501B, shown in a disassembled state, in accordance with at least some embodiments.

FIG. 5E is a schematic end view of the fixed blender 501B and the collar 503B of the adjustable ambient air-oxygen blender 500B, in accordance with at least some embodiments.

Referring now to FIGS. 5B and 5E, in accordance with at least some embodiments, the fixed blender 501B and the collar 503B are similar to the fixed blender 501 and the collar 503, respectively, of the adjustable ambient air-oxygen blender 500 (except where otherwise noted, like reference numerals that differ only in that one is succeeded by the letter "B" are used to indicate like or similar elements) except that the fixed blender 501B and the collar 503B of the adjustable ambient air-oxygen blender 500B each have ribs, e.g., rib 362B (FIG. 5E) and rib 364B (FIG. 5E), respectively, so that the fixed blender 501B can be inserted into the collar 503B and the ribs can releasably secure the collar 503B at any of various positions so that the air entrainment ports, e.g., air entrainment port 544B, can be covered to various extents.

The above ability to control the amount of ambient air that enters the fixed blender 501B to mix into the flowing oxygen provides the ability to change the air-oxygen mixture. The mixture is thus adjustable without any need to stop the flow of oxygen, dismantle a blender from the system, connect a new blender and then resume the flow of oxygen.

The plurality of ribs on the fixed blender 501B, e.g., rib 562B, may extend radially outward (e.g., as shown) at least in part or may have any other suitable shape(s) and/or positioning(s). Likewise, the plurality of ribs on the collar 503B, e.g., rib 564B, may extend radially inward (e.g., as shown) at least in part or may have any other suitable shape(s) and/or positioning(s).

The plurality of ribs on the fixed blender 501B, e.g., rib 562B, and the plurality of ribs on the collar 503B, e.g., rib 564B, may be disposed parallel to (or at least substantially parallel to) the longitudinal axis 550B (e.g., as shown) or at any other suitable angle thereto or in any other suitable orientation(s).

As used herein, the term "substantially parallel" means "parallel +/−10 degrees, preferably parallel +/−5 degrees, more preferably parallel +/−1 degree."

The plurality of ribs, e.g., rib 562B, on the fixed blender 501B may be arranged in a rib array that extends at least in part in a circumferential direction, with successive ribs in the rib array being offset from one another at least in part in the circumferential direction. Successive ribs in the rib array may define a channel therebetween. The rib array as a whole may thus define a plurality of channels, e.g., channel 566B, that are offset from one another at least in part in a circumferential direction and interspersed with the plurality of ribs.

Likewise, the plurality of ribs, e.g., rib 564B, on the collar 503B may be arranged in a rib array that extends at least in part in a circumferential direction, with successive ribs in the rib array being offset from one another at least in part in the circumferential direction. Successive ribs in the rib array may define a channel therebetween. the rib array as a whole may thus define a plurality of channels, e.g., channel 568B, that are offset from one another at least in part in a circumferential direction and interspersed with the plurality of ribs.

The plurality of ribs on the fixed blender 501B may releasably engage the plurality of ribs on the collar 503B as follows.

With the fixed blender 501B and the collar 503B in one of the various relative positions with respect to the ribs, one or more of the plurality of ribs, e.g., rib 562B, of the fixed blender 501B may be positioned in one or more of the channels, e.g., channel 568B, defined by the ribs of the collar 503B to thereby create interference to restrict (at least in part) relative movement between the fixed blender 501B and the collar 503B. Likewise, one or more of the plurality of ribs, e.g., rib 564B, of the collar 503B may be positioned in one or more channel, e.g., channel 566B, defined by the ribs of the fixed blender 501B to thereby create interference to restrict (at least in part) relative movement between the fixed blender 501B and the collar 503B.

The fixed blender 501B and the collar 503B may be releasable from a relative positioning by application of suitable force(s) to the fixed blender 501B and/or the collar 503B.

In at least some embodiments, the fixed blender 501B and the collar 503B may have a snug fit and/or a friction fit.

In at least some embodiments, the fixed blender 501B and the collar 503B may include other structures (complementary or otherwise) that are not ribs but nonetheless have the capability to releasably engage one another and/or releasably secure the fixed blender 501B and the collar 503B in any of various relative positions with respect to the structures and permit relative movement upon application of suitable force(s) by a user (or otherwise) to the fixed blender 501B and/or the collar 503B.

In at least some embodiments, the fixed blender 501B may be provided with teeth and the collar 503B may be provided with one or more protrusion.

Figures 5C, 5F:
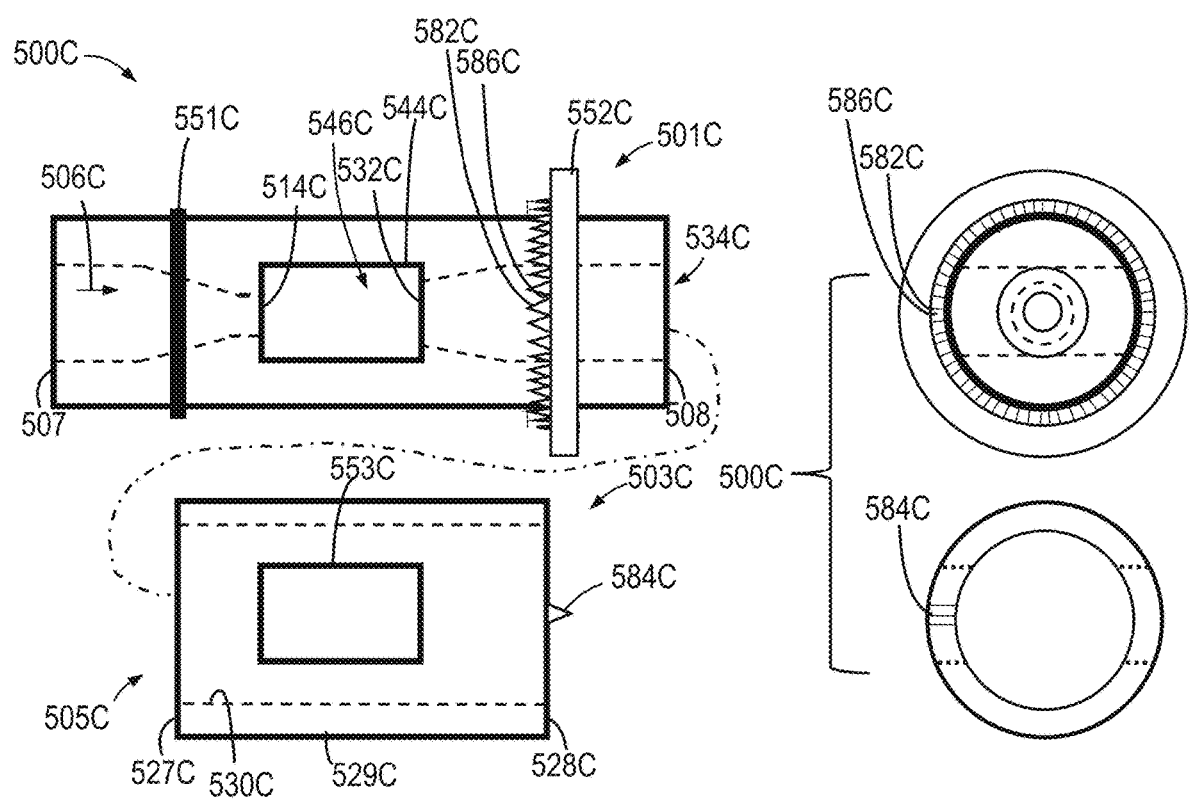
FIG. 5C is a schematic side view of a fixed blender and a collar of an adjustable ambient air-oxygen blender shown in a disassembled state, in accordance with at least some embodiments.
FIG. 5F is a schematic end view of the fixed blender and the collar of the adjustable ambient air-oxygen blender of FIG. 5C shown in a disassembled state, in accordance with at least some embodiments.

FIG. 5C is a schematic side view of an adjustable ambient air-oxygen blender 500C that includes a fixed blender 501C and a collar 503C that slides over the fixed blender 501C and movably couples to the fixed blender 501C, shown in a disassembled state, in accordance with at least some embodiments.

FIG. 5F is a schematic end view of the fixed blender 501C and the collar 503C of the adjustable ambient air-oxygen blender 500C, in accordance with at least some embodiments.

Referring now to FIGS. 5C and 5F, in accordance with at least some embodiments, the fixed blender 501C and the collar 503C are similar to the fixed blender 501B and the collar 503B, respectively, of the adjustable ambient air-oxygen blender 500B (except where otherwise noted, like reference numerals that differ only in that one is succeeded by the letter "C" instead of the letter "B" are used to indicate like or similar elements) except that the fixed blender piece 501C of the adjustable ambient air-oxygen blender 500C has teeth, e.g., tooth 582C, and the collar 503C has a single protrusion, e.g., protrusion 584C, so that the fixed blender 501C can be inserted into the collar 503C and the single protrusion, e.g., protrusion 584C, can releasably secure the collar 501C at any of various positions so that the air entrainment ports, e.g., air entrainment port 544C, can be covered to various extents.

The above ability to control the amount of ambient air that enters the fixed blender 501C to mix into the flowing oxygen provides the ability to change the air-oxygen mixture. The mixture is thus adjustable without any need to stop the flow of oxygen, dismantle a blender from the system, connect a new blender and then resume the flow of oxygen.

The plurality of teeth on the fixed blender 501C, e.g., tooth 582C, may extend in a longitudinal direction (e.g., as shown) at least in part or may have any other suitable orientation(s) and/or positioning(s). Likewise, the protrusion on the collar 503C, e.g., protrusion 584C, may extend in a longitudinal direction (e.g., as shown) at least in part or may have any other suitable orientation and/or positioning.

In at least some embodiments, the plurality of teeth on the fixed blender 501C, e.g., tooth 582C, are part of and/or extend from the stop 552C. The protrusion 584C may extend from the second end 528C of the collar 503C.

In at least some embodiments, the plurality of teeth, e.g., tooth 582C, on the fixed blender 501C and the protrusion, e.g., protrusion 584C, on the collar 503C may be disposed parallel to (or at least substantially parallel to) the longitudinal axis 550B (e.g., as shown) or at any other suitable angle thereto or in any other suitable orientation(s).

The plurality of teeth, e.g., tooth 582C, on the fixed blender 501C may be arranged in a tooth array that extends at least in part in a circumferential direction, with successive teeth in the tooth array being offset from one another at least in part in the circumferential direction. Successive teeth in the tooth array may define a channel therebetween. In view thereof, the tooth array as a whole may collectively define a plurality of channels, e.g., channel 586C, that are offset from one another at least in part in a circumferential direction and interspersed with the plurality of teeth.

The protrusion, e.g., protrusion 584C, on the collar 503C may releasably engage the plurality of teeth on the fixed blender 501C as follows.

With the fixed blender 501C and the collar 503C in one of the various relative positions, the protrusion, e.g., protrusion 584C, of the collar 503C may be positioned in one or more channel, e.g., channel 586C, defined by the teeth of the fixed blender 501C to thereby create interference to restrict (at least in part) relative movement between the fixed blender 501C and the collar 503C.

The fixed blender 501C and the collar 503C may be releasable from a relative position by application of suitable force(s) to the fixed blender 501C and/or the collar 503C.

In at least some embodiments, the fixed blender 501C and the collar 503C may have a snug fit and/or a friction fit.

In at least some embodiments, the collar 503C may include the plurality of teeth, e.g., tooth 582C, and the fixed blender 501 may include the protrusion, e.g., protrusion 584C.

Figure 6A:
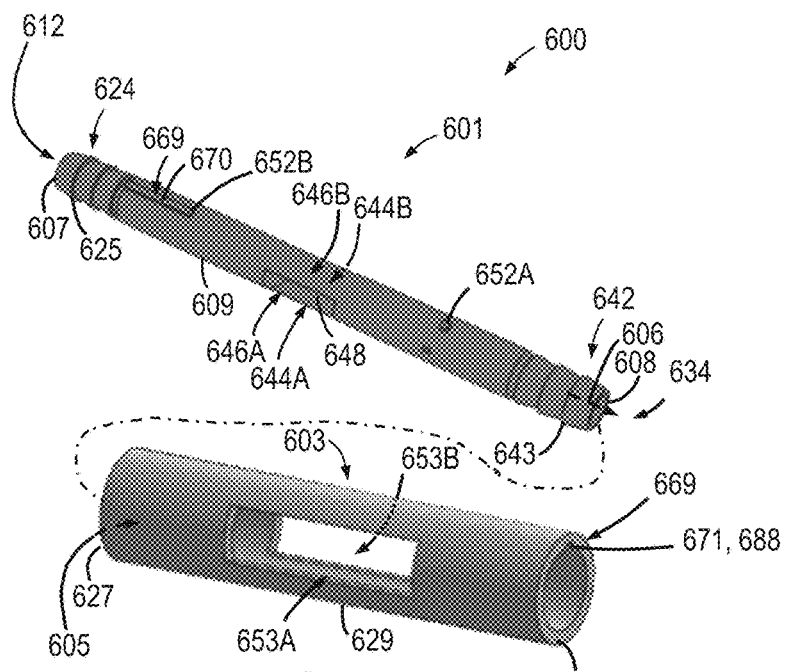
FIG. 6A is a perspective view of an adjustable ambient air-oxygen blender, which includes a fixed air blender and a collar, in a disassembled state, in accordance with at least some embodiments.
Figure 6B:
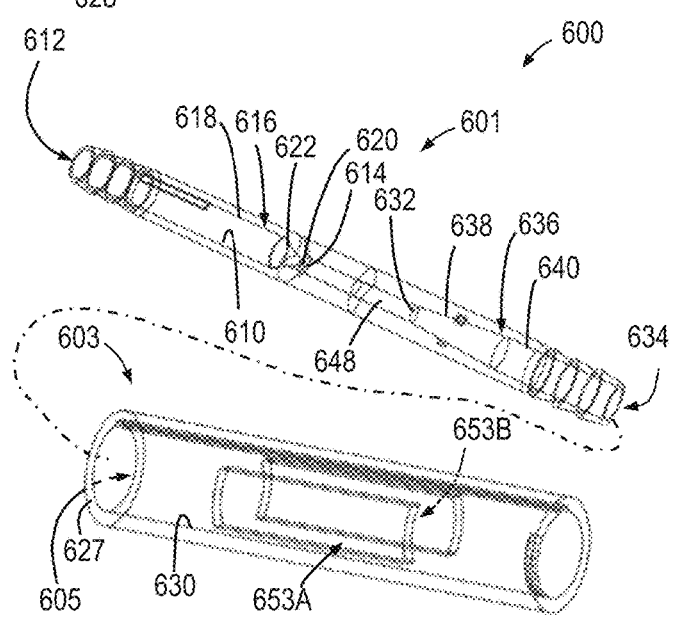
FIG. 6B is a rendering with transparency of a 3D computer model of the adjustable ambient air-oxygen blender of FIG. 6A, in a disassembled state, in accordance with at least some embodiments.
Figure 6C:
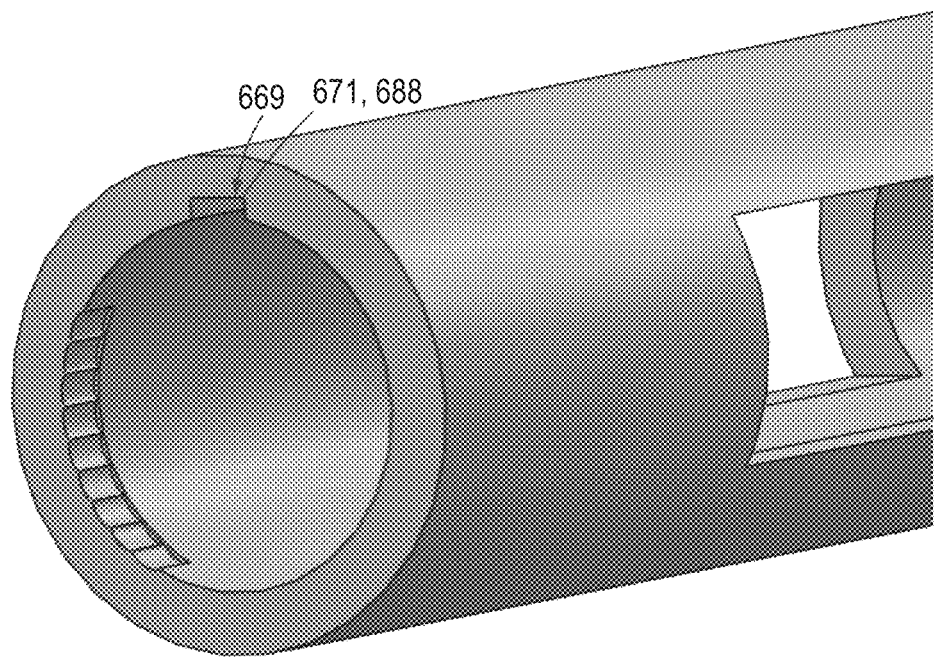
FIG. 6C is an enlarged perspective view of a portion of the collar of the adjustable ambient air-oxygen blender of FIG. 6A, in accordance with at least some embodiments.
Figure 6D:
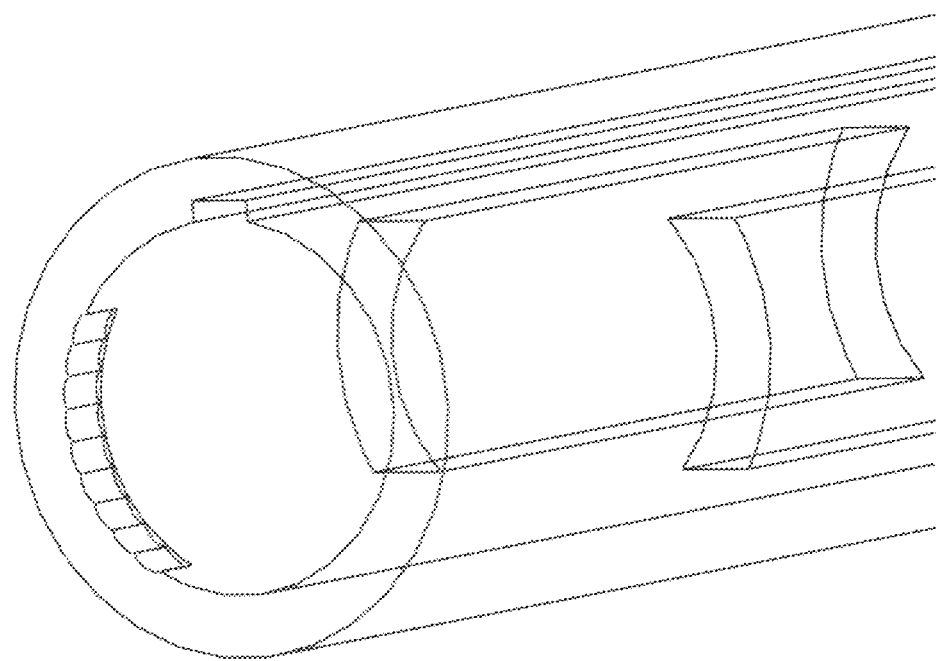
FIG. 6D is an enlarged rendering with transparency of a portion of the 3D computer model of the collar of the adjustable ambient air-oxygen blender of FIG. 6A, in accordance with at least some embodiments.
Figure 6E:
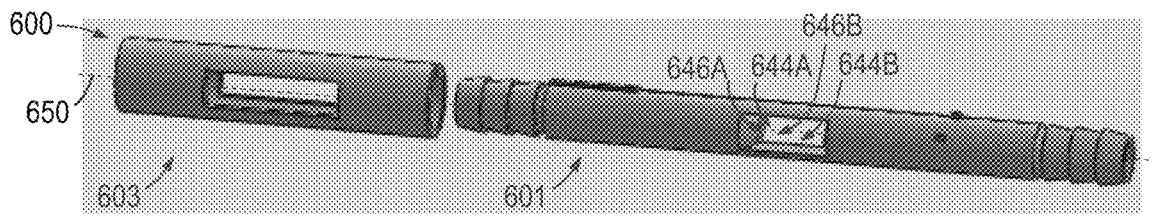
FIG. 6E is a perspective view of the adjustable ambient air-oxygen blender of FIG. 6A, in a disassembled state but with the fixed air blender and the collar of the adjustable ambient air-oxygen blender aligned with one another, in accordance with at least some embodiments.
Figure 6F:
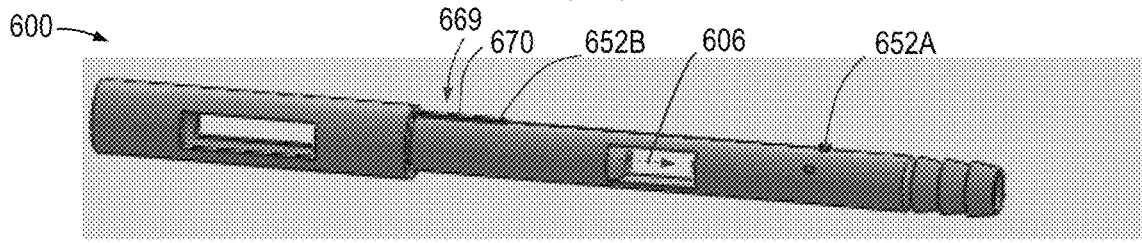
FIG. 6F is a perspective view of the adjustable ambient air-oxygen blender of FIG. 6A in a partly assembled state, in accordance with at least some embodiments.
Figure 6G:
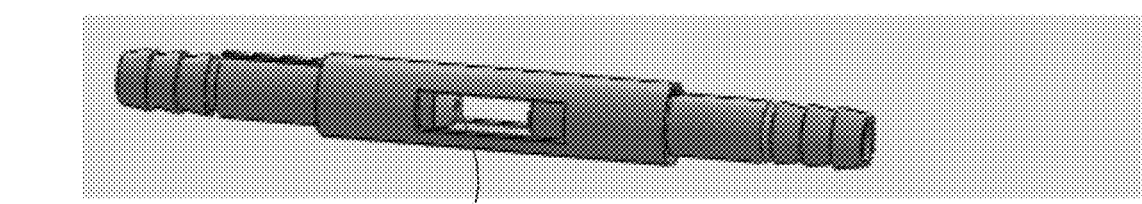
FIG. 6G is a perspective view of the adjustable ambient air-oxygen blender of FIG. 6A, in an assembled state, with the fixed air blender and the collar in a first relative positioning, in accordance with at least some embodiments.
Figure 6H:
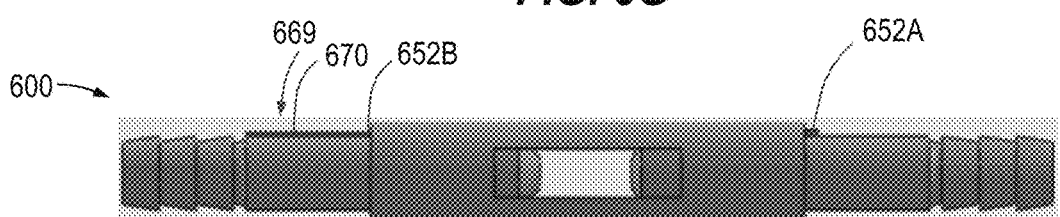
FIG. 6H is a side view of the adjustable ambient air-oxygen blender of FIG. 6A, in an assembled state, with the fixed air blender and the collar in a first relative positioning, in accordance with at least some embodiments.
Figure 6I:
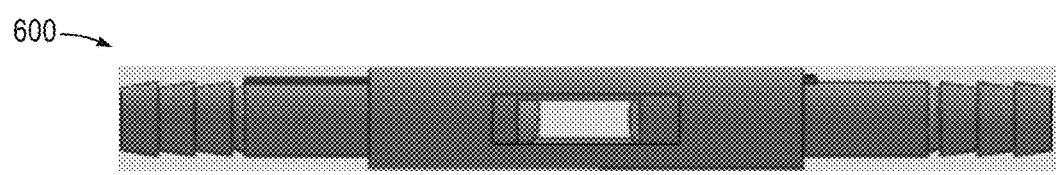
FIG. 6I is a side view of the adjustable ambient air-oxygen blender of FIG. 6A, with the fixed air blender and the collar in a second relative positioning, in accordance with at least some embodiments.
Figure 6J:
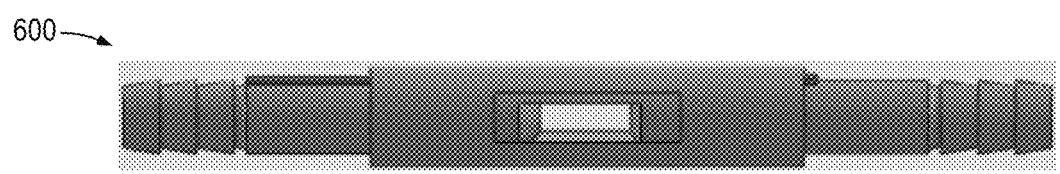
FIG. 6J is a side view of the adjustable ambient air-oxygen blender of FIG. 6A, with the fixed air blender and the collar in a third relative positioning, in accordance with at least some embodiments.
Figure 6K:
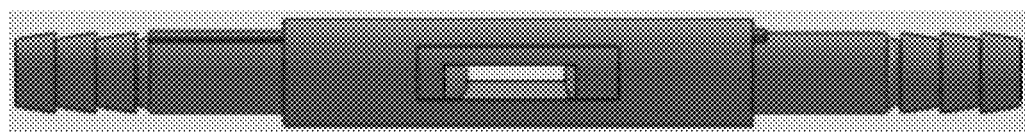
FIG. 6K is a side view of the adjustable ambient air-oxygen blender of FIG. 6A, with the fixed air blender and the collar in a fourth relative positioning, in accordance with at least some embodiments.
Figure 6L:
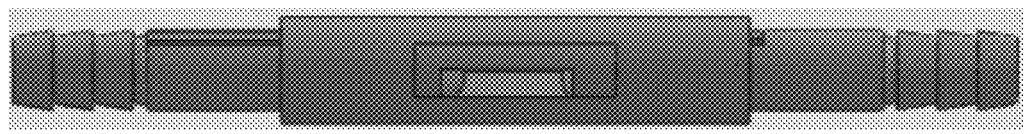
FIG. 6L is a side view of the adjustable ambient air-oxygen blender of FIG. 6A, with the fixed air blender and the collar in a fifth relative positioning, in accordance with at least some embodiments.
Figure 6M:
FIG. 6M is a side view of the adjustable ambient air-oxygen blender of FIG. 6A, with the fixed air blender and the collar in a sixth relative positioning, in accordance with at least some embodiments.
Figure 6N:
FIG. 6N is a side view of the adjustable ambient air-oxygen blender of FIG. 6A, with the fixed air blender and the collar in a seventh relative positioning, in accordance with at least some embodiments.
Figure 6O:
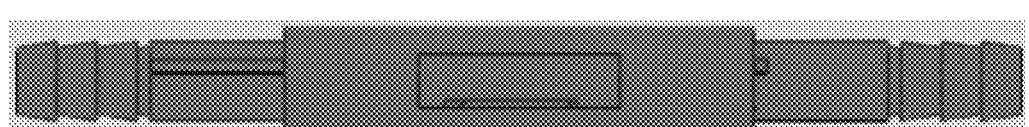
FIG. 6O is a side view of the adjustable ambient air-oxygen blender of FIG. 6A, with the fixed air blender and the collar in an eighth relative positioning, in accordance with at least some embodiments.
Figure 6P:
FIG. 6P is a side view of the adjustable ambient air-oxygen blender of FIG. 6A, with the fixed air blender and the collar in a ninth relative positioning, in accordance with at least some embodiments.
Figure 6Q:
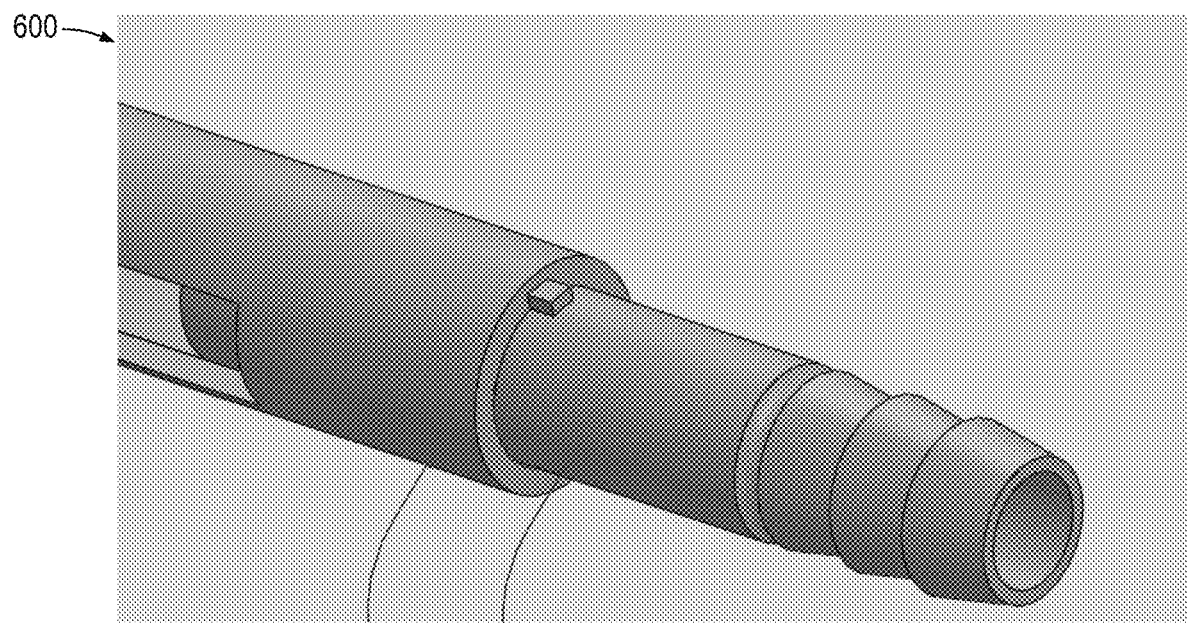
FIG. 6Q is an enlarged perspective view of a portion of the adjustable ambient air-oxygen blender of FIG. 6A in accordance with at least some embodiments.
Figure 6R:
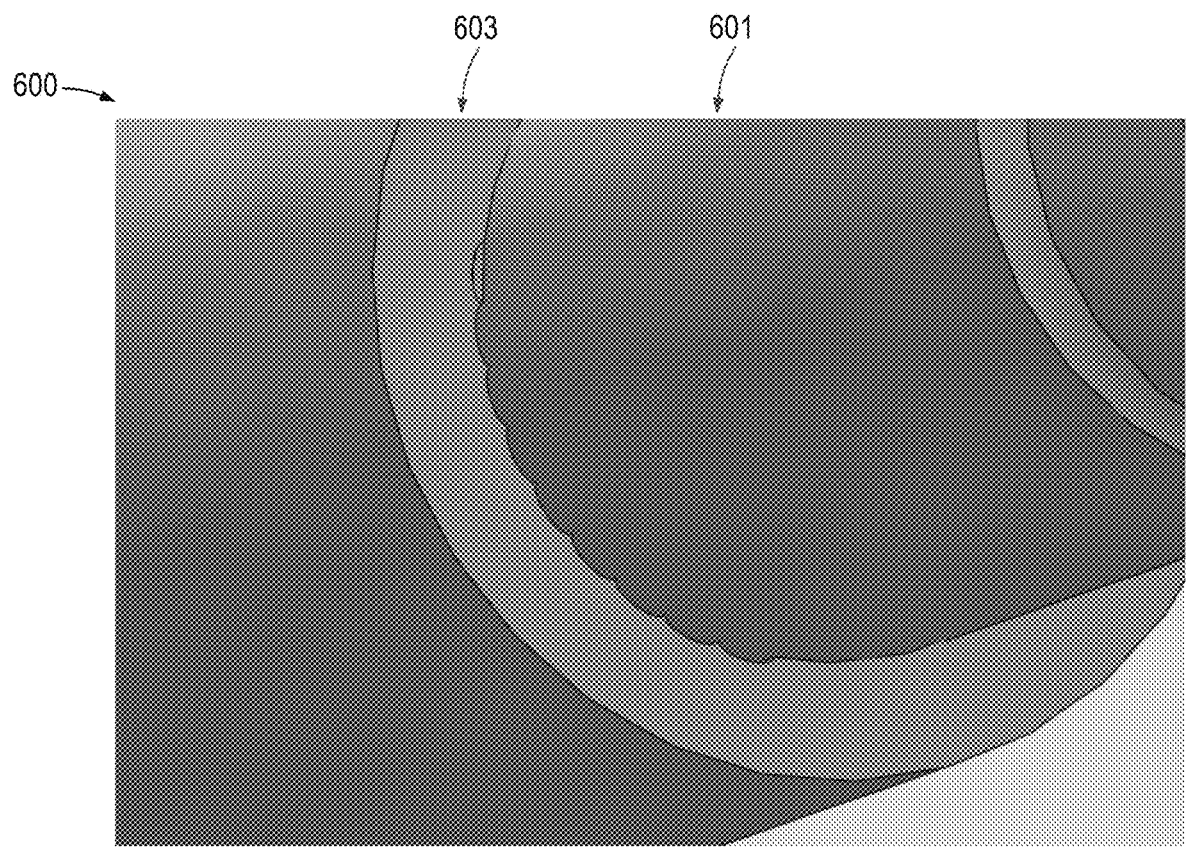
FIG. 6R is an enlarged perspective view of a portion of the adjustable ambient air-oxygen blender of FIG. 6A, in accordance with at least some embodiments.

FIGS. 6A-6R show views of an adjustable ambient air-oxygen blender having a fixed blender 600 and a collar piece 603 that movably couples thereto, in accordance with at least some embodiments.

In particular, FIG. 6A is a perspective view of the adjustable ambient air-oxygen blender 600, in a disassembled state, in accordance with at least some embodiments.

FIG. 6B is a rendering, with transparency of a 3D computer model of the adjustable ambient air-oxygen blender 600, in a disassembled state, in accordance with at least some embodiments.

FIG. 6C is an enlarged perspective view of a portion of the collar 603 of the adjustable ambient air-oxygen blender 600, in accordance with at least some embodiments.

FIG. 6D is an enlarged rendering with transparency of a portion of the 3D computer model of the collar 603 of the adjustable ambient air-oxygen blender 600, in accordance with at least some embodiments.

FIG. 6E is a perspective view of the adjustable ambient air-oxygen blender 600, in a disassembled state but with the fixed air blender 601 and the collar 603 of the adjustable ambient air-oxygen blender 600 aligned with one another, in accordance with at least some embodiments.

Referring now to FIGS. 6A-6E, in accordance with at least some embodiments, the collar 603 may define an opening 605 to movably receive the fixed blender 601 to movably couple the fixed blender 601 and the collar 603. In at least some embodiments, the fixed blender 501 and the collar 503 are rotatably coupled.

The adjustable ambient air-oxygen blender 600 defines a gas flow path 606 (FIG. 6F) that extends through the fixed air blender 601.

The fixed blender 601 may have a first end 607, a second end 608, an outer surface 609 and an inner surface 610.

The fixed blender 601 defines an inlet 612, a nozzle 614 in fluid communication with the inlet 612, a channel 616 extending between the inlet 612 and the nozzle 614 (FIGS. 6B, 6G), an orifice 632 (FIG. 6B), an oxygen-air mixture outlet 634 in fluid communication with the orifice 632, and a channel 636 extending between the orifice 632 and the oxygen-air mixture outlet 634. The inlet 612 may be disposed at the first end 607 of the fixed blender 601 and/or at a first end of the gas flow path 606. The nozzle 614 is in fluid communication with and downstream of the inlet 612 and may have a cross sectional area that is less than a cross sectional area of the inlet 612. The channel 616 may have one or more spans of uniform cross-sectional diameter, e.g., a span 618 and a span 620, and/or one or more spans of decreasing cross sectional diameter, e.g., a span 622 having a uniformly decreasing or otherwise tapered contour. The orifice 632 (FIG. 6B) is in fluid communication with and downstream of the nozzle 614 (FIGS. 6B, 6G) and may have a cross sectional area that is greater than the cross-sectional area of the nozzle 614. The oxygen-air mixture outlet 634, which may be disposed at a second end of the gas flow path 606, is downstream of the orifice 632 and may have a cross sectional area that is greater than the cross-sectional area of the orifice 632. The channel 636 may have one or more spans of increasing cross sectional diameter, e.g., a span 638 having a uniformly increasing or otherwise tapered contour, and/or one or more spans of uniform cross-sectional diameter, e.g., a span 640.

The fixed blender 601 may include a first connector 624, which may be configured to be releasably or otherwise connected to a tube or other gas line that is coupled (directly and/or indirectly) to an external reservoir (not shown) (and/or other source) of oxygen (or other gas(es)) to be supplied to the adjustable ambient air-oxygen blender 600 and to be mixed with ambient air. The first connector 624 may include one or more barbs, e.g., barb 625, which may assist in securing (releasably or otherwise) a tube or other gas line thereto. The first connector 624 may be disposed at, proximal to and/or otherwise toward the first end 607 of the fixed blender 501.

The fixed blender 601 may further include a second connector 642, which may be configured to be releasably or otherwise connected to a tube or other gas line that is coupled (directly and/or indirectly) to a nasal or other breathing apparatus and/or other destination to which a mixture from the adjustable ambient air-oxygen blender 600 is to be supplied. The second connector 642 may be disposed at, proximal to and/or otherwise toward the second end 608 of the fixed blender 601. The second connector 642 may include one or more barbs, e.g., barb 643, which may assist in securing (releasably or otherwise) a tube or other gas line thereto.

In at least some embodiments, any of the adjustable ambient air-oxygen blenders disclosed herein, may include one or more connector, which may be the same as and/or similar to one or more of the connectors 624, 642 or otherwise.

The fixed blender 601 further defines at least one ambient air entrainment port, e.g., ambient air entrainment ports 644A (in FIG. 6A, defined by the near side of the adjustable ambient air-oxygen blender 600), 644B ((in FIG. 6A, defined by the far side of the adjustable ambient air-oxygen blender 600), that provides at least one flow path, e.g., flow paths 646A (in FIG. 6A, through the near side of the adjustable ambient air-oxygen blender 600), 646B (in FIG. 4A, through the far side of the adjustable ambient air-oxygen blender 600), for ambient air to enter the adjustable ambient air-oxygen blender 600. The at least one ambient air entrainment port, e.g., ambient air entrainment ports 644A, 644B, may have a rectangular cross section (e.g., as shown) or any other suitable configuration.

The fixed blender 601 may further define an ambient air entrainment chamber 648 in fluid communication with the nozzle 614 to receive oxygen that exits therefrom, and in fluid communication with the at least one ambient air entrainment port, e.g., ambient air entrainment ports 644A, 644B, to receive ambient air that enters the adjustable ambient air-oxygen blender 600 therethrough. In at least some embodiments, including but not limited to the illustrated embodiment, the ambient air entrainment chamber 648 is disposed (at least in part) between the nozzle 614 and the orifice 632 and/or in fluid communication between the nozzle 614 and the orifice 632.

The adjustable ambient air-oxygen blender 600 may have a longitudinal axis 650 (FIG. 6E), which may extend in a longitudinal direction. The fixed blender 601 and/or collar 603 may be disposed along and/or about the longitudinal axis 650 and/or may have a longitudinal axis coincident (or substantially coincident) with the longitudinal axis 650.

The flow path 606 (FIG. 6F) (or one or more portions thereof) may be disposed along and/or about the longitudinal axis 650 and/or may have a longitudinal axis coincident (or substantially coincident) with the longitudinal axis 650.

The fixed blender 601 may further include one or more stop, e.g., stops 652A, 652B (FIGS. 6A, 6H). In at least some embodiments, in the assembled state (e.g., FIG. 6H) the one or more stops, e.g., stops 652A, 652B, limit travel by the collar 603 in one or more longitudinal directions, e.g. in a direction toward the second end 608 of the fixed blender 601 and in a direction toward the first end 607 of the fixed blender 601, respectively.

In at least some embodiments, any of the adjustable ambient air-oxygen blenders disclosed herein may include one or more stops, which may be the same as and/or similar to the one or more stops, e.g., stops 652A, 652B, or otherwise.

The collar 603 may have a first end 627, a second end 628, an outer surface 629 and an inner surface 630.

As stated above, the collar 603 may define an opening 605 to slidably or otherwise receive the fixed blender 601 to movably couple the fixed blender 601 and the collar 603. In at least some embodiments, the fixed blender 601 and the collar 603 are rotatably coupled.

The collar 603 may further define at least one opening, e.g., openings 653A, 653B (FIGS. 6A, 6B), which may be longitudinally aligned (at least in part) with the at least one ambient air entrainment port, e.g., the ambient air entrainment ports 644A, 644B, so as to provide at least one flow path through which ambient air may flow to reach the at least one ambient air entrainment port, e.g., the ambient air entrainment ports 644A, 644B, if the angular position of the collar 603 relative to the fixed blender 601 is such that the at least one opening, e.g., openings 653A, 653B, and the at least one ambient air entrainment port, e.g., the ambient air entrainment ports 644A, 644B, are radially aligned (at least in part). The at least one opening, e.g., openings 653A, 653B, may have a rectangular cross section (e.g., as shown) or any other suitable configuration.

In at least some embodiments, including but not limited to the illustrated embodiment, the collar 603 slides over the first end 607 of the fixed blender 601 and fits snugly to it to releasably secure the collar 603 to the fixed blender 601 and so that the collar 603 can be rotated (upon application of suitable force(s) by a user (or otherwise) to the fixed blender 601 and/or the collar 603) to different angular positions relative to the fixed blender 601 to cover different areas of the one or more air-entrainment ports, e.g., air-entrainment ports 644A, 644B, of the fixed blender 601 to limit (to different extents) the amount of ambient air that enters the fixed blender 601 to mix into the flowing oxygen.

Thus, the fixed blender 601 and/or collar 603 may be rotated relative to the other to cause the collar 603 to cover a variable size extent of the at least one ambient air entrainment port, e.g., ambient air entrainment ports 644A, 644B, and thereby limit to a variable extent the amount of ambient air that enters the adjustable ambient air-oxygen blender 600 through the at least one ambient air entrainment port, e.g., ambient air entrainment ports 644A, 644B.

The above ability to control the amount of ambient air that enters the fixed blender 601 to mix into the flowing oxygen provides the ability to change the air-oxygen mixture. The mixture is thus adjustable without any need to stop the flow of oxygen, dismantle a blender from the system, connect a new blender and then resume the flow of oxygen.

In at least some embodiments, the snug fit results from an interface between the outer surface 609 of the fixed blender 601 and the inner surface 630 of the collar 603.

The snug fit may be a friction fit (a type of interference fit) in which the fixed blender 601 and collar 603 are pressed together and thereafter movably coupled by friction at an interface of the collar 603 and the fixed blender 601.

At least some embodiments may employ a friction fit of any desired tightness. As is known, the characteristics of a friction fit depend at least in part on the amount of dimensional interference that is provided at the interface between the two parts. In at least some embodiments, a friction fit of any suitable tightness may be provided an interface between the fixed blender 601 and the collar 603.

In at least some embodiments, a snug fit and/or a friction fit provides resistance to relative movement (longitudinal and/or rotational) between the collar 603 and fixed blender 601 to thereby movably couple and/or releasably secure the collar 603 to the fixed blender 601.

The collar 603 may define one or more channel (or other recessed portion), e.g., channel 688 (FIG. 6C), that slidably or otherwise receives one or more of the one or more stops, e.g., the stop 652B, to prevent such stop(s) from interfering with the collar 603 slidably or otherwise receiving the fixed blender 601 during assembly.

The one or more channel (or other recessed portion), e.g., channel 688 (FIG. 6C), may extend in a longitudinal direction and/or parallel (or at least substantially parallel) to the longitudinal axis 650 (e.g., as shown) or may have any other suitable shape(s) and/or orientation(s).

The fixed blender 601 and/or the collar 603 (or one or more portions of the fixed blender 601 and/or the collar 603) may have cylindrical shape(s) (e.g. as shown), rectangular shape(s) or any other suitable shape(s).

FIGS. 6F-6P show views of the adjustable ambient air-oxygen blender 600 as an assembly of the two pieces (the fixed blender 601 and the collar 603). In accordance with at least some embodiments, in this design and in at least some other embodiments, once in position, the collar 603 can be rotated to cover the air entrainment ports, e.g., ambient air entrainment ports 644A, 644B, to various extents to allow different amounts of air to mix into the flowing oxygen. The ability to control the amount of ambient air that enters the fixed blender 601 to mix into the flowing oxygen provides the ability to change the air-oxygen mixture. The mixture is thus adjustable without any need to stop the flow of oxygen, dismantle a blender from the system, connect a new blender and then resume the flow of oxygen.

In particular, FIG. 6F is a perspective view of the adjustable ambient air-oxygen blender 600 in a partly assembled state, in accordance with at least some embodiments.

FIG. 6G is a perspective view of the adjustable ambient air-oxygen blender 600, in an assembled state, with the fixed air blender 601 and the collar 603 in a first relative positioning, in accordance with at least some embodiments.

FIG. 6H is a side view of the adjustable ambient air-oxygen blender 600, in an assembled state, with the fixed air blender 601 and the collar 603 in the first relative positioning, in accordance with at least some embodiments.

FIG. 6I is a side view of the adjustable ambient air-oxygen blender 600, with the fixed air blender 601 and the collar 603 in a second relative positioning, in accordance with at least some embodiments.

FIG. 6J is a side view of the adjustable ambient air-oxygen blender 600, with the fixed air blender 601 and the collar 603 in a third relative positioning, in accordance with at least some embodiments.

FIG. 6K is a side view of the adjustable ambient air-oxygen blender 600, with the fixed air blender 601 and the collar 603 in a fourth relative positioning, in accordance with at least some embodiments.

FIG. 6L is a side view of the adjustable ambient air-oxygen blender 600, with the fixed air blender 601 and the collar 603 in a fifth relative positioning, in accordance with at least some embodiments.

FIG. 6M is a side view of the adjustable ambient air-oxygen blender 600, with the fixed air blender 601 and the collar 603 in a sixth relative positioning, in accordance with at least some embodiments.

FIG. 6N is a side view of the adjustable ambient air-oxygen blender 600, with the fixed air blender 601 and the collar 603 in a seventh relative positioning, in accordance with at least some embodiments.

FIG. 6O is a side view of the adjustable ambient air-oxygen blender 600, with the fixed air blender 601 and the collar 603 in an eighth relative positioning, in accordance with at least some embodiments.

FIG. 6P is a side view of the adjustable ambient air-oxygen blender 600, with the fixed air blender 601 and the collar 603 in a ninth relative positioning, in accordance with at least some embodiments.

FIG. 6Q is an enlarged perspective view of a portion of the adjustable ambient air-oxygen blender 600 in accordance with at least some embodiments.

FIG. 6R is an enlarged perspective view of a portion of the adjustable ambient air-oxygen blender 600 in accordance with at least some embodiments.

Referring first to FIG. 6F, the fixed blender 601 and the collar 603 may collectively define one or more guide, e.g., guide 669 (FIGS. 6A, 6C, 6F), to ensure that the fixed blender 601 and the collar 603 have a desired angular orientation during and/or after assembly of the adjustable ambient air-oxygen blender 600. In at least some embodiments, the one or more guide, e.g., guide 669, ensures that the fixed blender 601 and the collar 603 have a desired initial angular orientation so that there is a desired initial angular orientation between the at least one air-entrainment port, e.g., air entrainment ports 644A, 644B, of the fixed blender 601 and the at least one opening, e.g., openings 653A, 653B, of the collar 603.

The one or more guide, e.g., guide 669 (FIGS. 6A, 6C, 6F), may comprise a first structure 670 (FIGS. 6A, 6F) defined by the fixed blender 601 and a second structure 671 (FIG. 6C) (complementary or otherwise to the first structure 670) that is defined by the collar 603 and engages with the first structure 670 at least during assembly of the adjustable ambient air-oxygen blender 600.

In at least some embodiments, the first structure 670 comprises a rail or other raised portion and the second structure 671 comprises a channel or other recessed portion (e.g., as shown) that receives the rail or other raised portion.

In at least some other embodiments, the first structure 670 comprises a channel or other recessed portion and the second structure 671 comprises a rail or other raised portion.

The channel or other recessed portion and the rail or other raised portion may each extend in a longitudinal direction and/or parallel (or at least substantially parallel) to the longitudinal axis 650 (e.g., as shown) or may have any other suitable shape(s) and/or orientation(s). The rail or other raised portion may or may not be continuous and/or uniform and may or may not have a same length as the channel. In at least some embodiments, the rail or other raised portion may comprise a stub or a plurality of stubs (of same or different lengths).

In at least some embodiments, any of the adjustable ambient air-oxygen blenders disclosed herein may include one or more guide, which may be the same as and/or similar to the one or more guide, e.g., guide 669, or otherwise.

Referring now to FIGS. 6G-6P, with the fixed air blender 601 and the collar 603 in the first relative positioning, the at least one opening, e.g., openings 653A, 653B, of the collar 603 have a first angular offset (shown as zero) from the at least one ambient air-entrainment port, e.g., air entrainment ambient ports 644A, 644B, such that the collar covers a first extent (shown as zero) of the at least one ambient air-entrainment port, a first amount of ambient air reaches the at least one ambient air-entrainment port and the mixture has a first percentage of oxygen.

In the second relative positioning, the at least one opening, e.g., openings 653A, 653B, of the collar 603 has a second angular offset from the at least one ambient air-entrainment port, e.g., ambient air entrainment ports 644A, 644B, the collar covers a second extent of the at least one ambient air-entrainment port, a second amount of ambient air reaches the at least one ambient air-entrainment port and the mixture has a second percentage of oxygen.

The second angular offset is greater than the first angular offset and as a result the second extent covered by the collar is greater than the first extent. The second amount of ambient air that reaches the at least one ambient air-entrainment port is thus less than the first amount of ambient air that reaches the at least one ambient air-entrainment port, and the second percentage of oxygen in the mixture is thus greater than the first percentage of oxygen in the mixture.

In the third relative positioning, the at least one opening, e.g., openings 653A, 653B, of the collar 603 has a third angular offset from the at least one ambient air-entrainment port, e.g., ambient air entrainment ports 644A, 644B, the collar covers a third extent of the at least one ambient air-entrainment port, a third amount of ambient air reaches the at least one ambient air-entrainment port and the mixture has a third percentage of oxygen.

The third angular offset is greater than the second angular offset and as a result, the third extent covered by the collar is greater than the second extent. The third amount of ambient air that reaches the at least one ambient air-entrainment port is thus less than the second amount of ambient air that reaches the at least one ambient air-entrainment port, and the third percentage of oxygen in the mixture is thus greater than the second percentage of oxygen in the mixture.

And so on.

The mixture is thus adjustable without any need to stop the flow of oxygen, dismantle a blender from the system, connect a new blender and then resume the flow of oxygen.

In at least some embodiments, it may be desirable for relative positioning to be maintained unless it is determined that it should be changed and appropriate force(s) are applied to do so. It at least some embodiments, a snug fit and/or friction fit may accomplish such at least to a desired extent.

In at least some embodiments, the fixed blender 601 and the collar 606 may be provided with structures (complementary or otherwise) that releasably engage one another.

In at least some embodiments, the fixed blender 601 and the collar 603 may each include ribs, which may be the same as and/or similar to the ribs 562B and 564B, respectively, described above with respect to the adjustable ambient air-oxygen blender 500B (FIG. 5B).

In at least some embodiments, the fixed blender 601 and the collar 603 may include teeth and a protrusion, respectively, which may be the same as and/or similar to the teeth 582C and 584C, respectively, described above with respect to the adjustable ambient air-oxygen blender 500C (FIG. 5C).

Figure 7A:
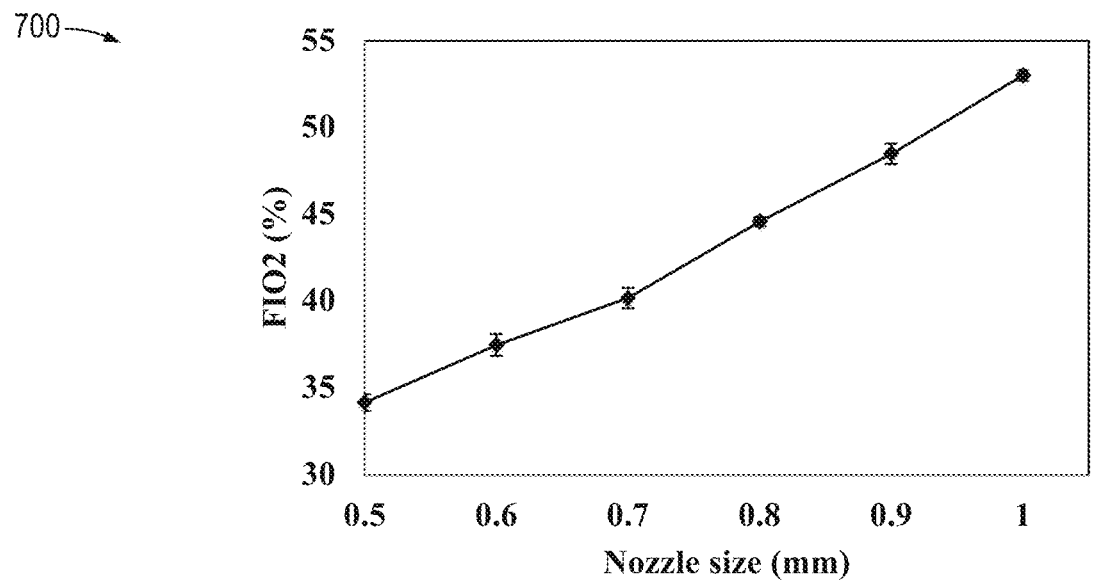
FIG. 7A is a graph illustrating a fraction of inspired oxygen ($FiO_2$) that may be provided by an ambient air-oxygen blender as a function of nozzle (Venturi nozzle) diameter size, with a fixed outlet orifice diameter size, in accordance with at least some embodiments.

FIG. 7A is a graph 700 illustrating a fraction of inspired oxygen (FiO2) that may be provided by an ambient air-oxygen blender as a function of nozzle (Venturi nozzle) diameter size, with a fixed outlet orifice diameter size, in accordance with at least some embodiments.

Referring to FIG. 7A, the graph shows that the fraction of inspired oxygen (FiO2) that was observed in a mixture exiting an ambient air-oxygen blender having an outlet orifice diameter of 2.0 mm increased linearly or at least substantially linearly from 34.2%±1.2% to 53.0%±0.7% as the nozzle diameter of the ambient air-oxygen blender was increased from 0.5 mm to 1.0 mm.

The flow rate for the test and for each of the tests described below, unless noted otherwise, was 1 Liters/min (L/min) and the temperature was 20° C.

Figure 7B:
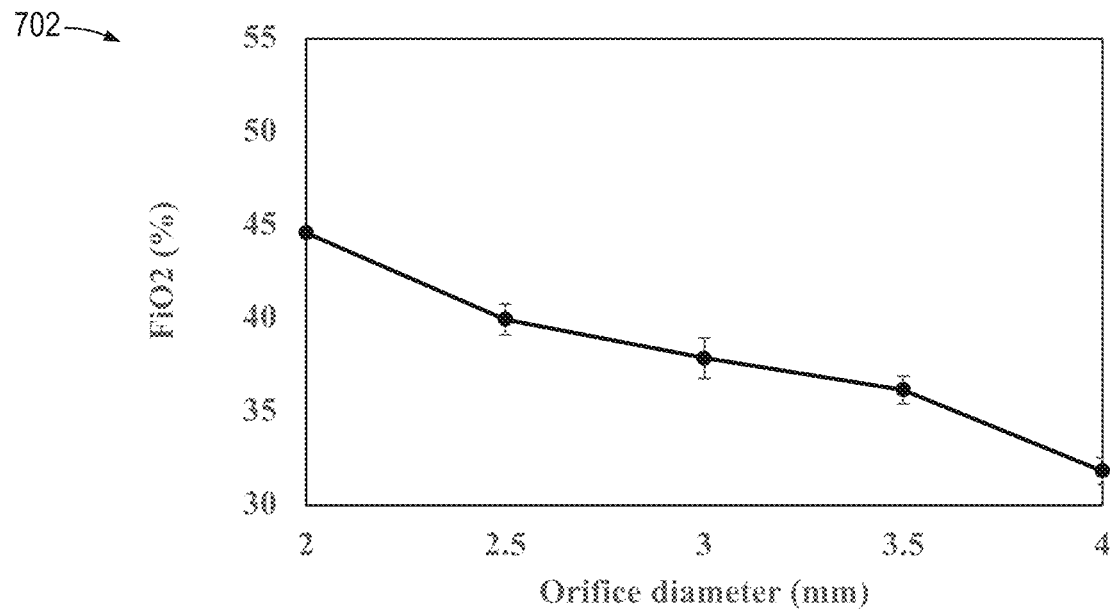
FIG. 7B is a graph illustrating a fraction of inspired oxygen (FiO2) that may be provided by an ambient air-oxygen blender as a function of outlet orifice diameter size, with a fixed nozzle (Venturi nozzle) diameter size, in accordance with at least some embodiments.

FIG. 7B is a graph 702 illustrating a fraction of inspired oxygen (FiO2) that may be provided by an ambient air-oxygen blender as a function of outlet orifice diameter size, with a fixed nozzle (Venturi nozzle) diameter size, in accordance with at least some embodiments.

Referring to FIG. 7B, the graph shows that the fraction of inspired oxygen (FiO2) that was observed in a mixture exiting an ambient air-oxygen blender having a nozzle diameter of 0.6 mm decreased monotonically from 44.6%±0.7% to 31.8%±1.7% as the outlet orifice diameter of the ambient air-oxygen blender was increased from 2.0 mm to 4.0 mm.

Figure 8A:
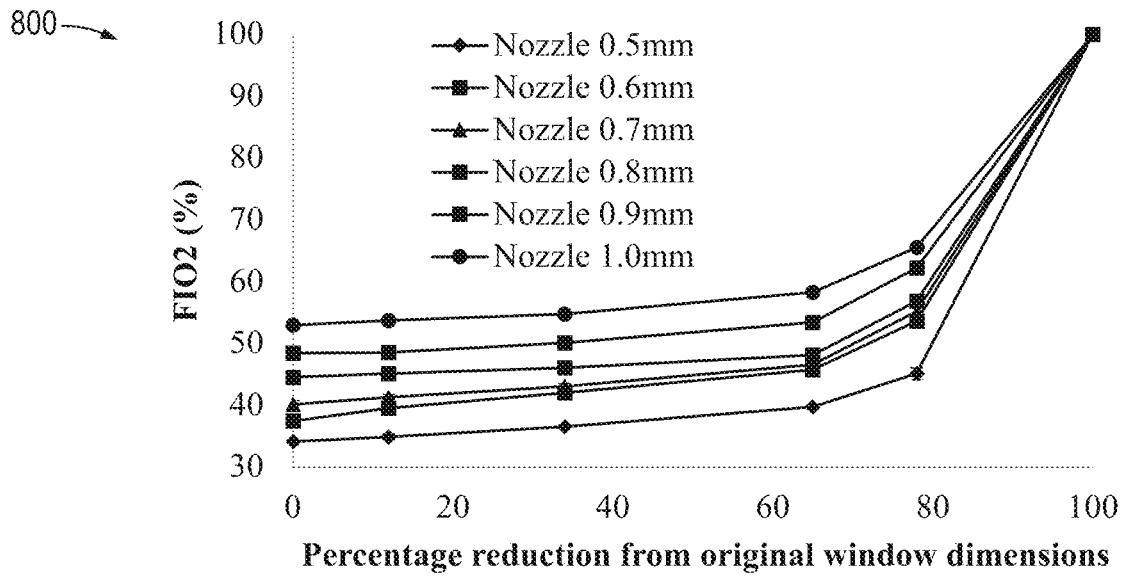
FIG. 8A is a graph illustrating a fraction of inspired oxygen (FiO2) that may be provided by an ambient air-oxygen blender as a function of a reduction in air-entrainment window cross-sectional area, for a plurality of different nozzle diameter sizes and a fixed outlet orifice diameter size, in accordance with at least some embodiments.

FIG. 8A is a graph 800 illustrating a fraction of inspired oxygen (FiO2) that may be provided by an ambient air-oxygen blender as a function of a reduction in air-entrainment window cross-sectional area, for a plurality of different nozzle diameter sizes and a fixed outlet orifice diameter size, in accordance with at least some embodiments.

Referring to FIG. 8A, the graph shows that the fraction of inspired oxygen (FiO2) that was observed in a mixture exiting an ambient air-oxygen blender having a nozzle diameter of 0.5 mm and an outlet orifice diameter of 2.0 mm increased exponentially from about 34% to 100% as the reduction in air-entrainment window cross-sectional area was increased from 0% to 100%. The fraction of inspired oxygen (FiO2) that was observed in a mixture exiting an ambient air-oxygen blender having a nozzle diameter of 0.6 mm and an outlet orifice diameter of 2.0 mm increased exponentially from about 37% to 100% as the reduction in air-entrainment window cross-sectional area was increased from 0% to 100%. The fraction of inspired oxygen (FiO2) that was observed in a mixture exiting an ambient air-oxygen blender having a nozzle diameter of 0.7 mm and an outlet orifice diameter of 2.0 mm increased exponentially from about 40% to 100% as the reduction in air-entrainment window cross-sectional area was increased from 0% to 100%. The fraction of inspired oxygen (FiO2) that was observed in a mixture exiting an ambient air-oxygen blender having a nozzle diameter of 0.8 mm and an outlet orifice diameter of 2.0 mm increased exponentially from about 45% to 100% as the reduction in air-entrainment window cross-sectional area was increased from 0% to 100%. The fraction of inspired oxygen (FiO2) that was observed in a mixture exiting an ambient air-oxygen blender having a nozzle diameter of 0.9 mm and an outlet orifice diameter of 2.0 mm increased exponentially from about 48% to 100% as the reduction in air-entrainment window cross-sectional area was increased from 0% to 100%. The fraction of inspired oxygen (FiO2) that was observed in a mixture exiting an ambient air-oxygen blender having a nozzle diameter of 1.0 mm and an outlet orifice diameter of 2.0 mm increased exponentially from about 50% to 100% as the reduction in air-entrainment window cross-sectional area was increased from 0% to 100%.

Figure 8B:
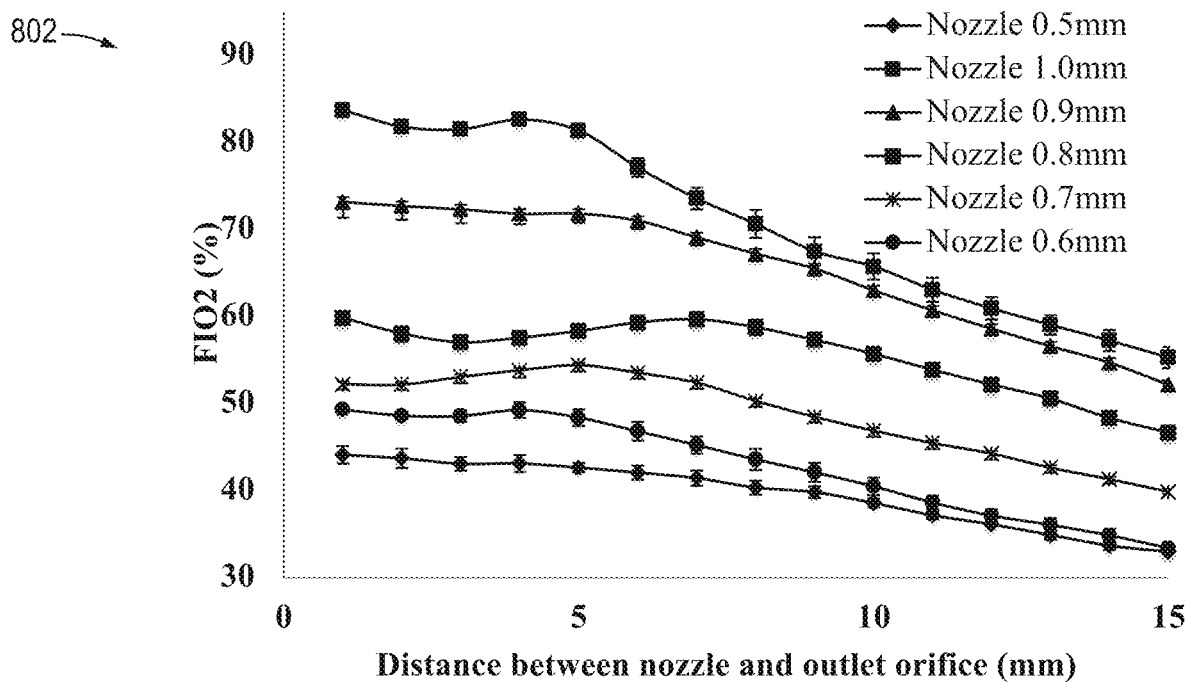
FIG. 8B is a graph illustrating a fraction of inspired oxygen (FiO2) as a function of a distance between a nozzle and an outlet orifice, for a plurality of different nozzle diameter sizes and a fixed outlet orifice diameter size, in accordance with at least some embodiments.

FIG. 8B is a graph 802 illustrating a fraction of inspired oxygen (FiO2) as a function of a distance between a nozzle and an outlet orifice, for a plurality of different nozzle diameter sizes and a fixed outlet orifice diameter size, in accordance with at least some embodiments.

Figure 9A:
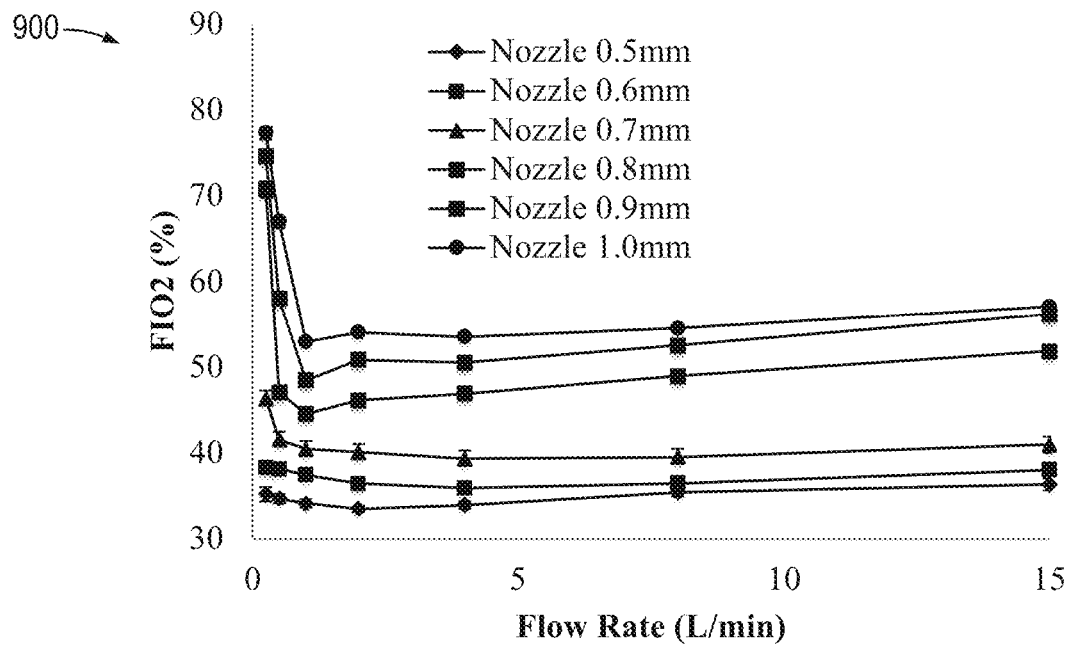
FIG. 9A is a graph illustrating a fraction of inspired oxygen (FiO2) as a function of a flow rate, for a plurality of different nozzle diameter sizes and a fixed outlet orifice diameter size, in accordance with at least some embodiments.

FIG. 9A is a graph 900 illustrating a fraction of inspired oxygen (FiO2) as a function of a flow rate, for a plurality of different nozzle diameter sizes and a fixed outlet orifice diameter size, in accordance with at least some embodiments.

Referring to FIG. 9A, the graph shows that the fraction of inspired oxygen (FiO2) that was observed in a mixture exiting an ambient air-oxygen blender having a nozzle diameter of 0.5 mm or 0.6 mm and an outlet orifice diameter of 2.0 mm decreased slightly as the flow rate increased from 0.25 L/min to 1 L/min. The fraction of inspired oxygen (FiO2) that was observed in a mixture exiting an ambient air-oxygen blender having a nozzle diameter of 0.7 mm, 0.8 mm, 0.9 mm or 1.0 mm and an outlet orifice diameter of 2.0 mm decreased significantly as the flow rate increased from 0.25 L/min to 1 L/min. For all nozzle diameter sizes, the fraction of inspired oxygen (FiO2) that was observed in a mixture exiting an ambient air-oxygen blender increased slightly with an increase in flow rate from 1 L/min to 15 L/min.

Figure 9B:
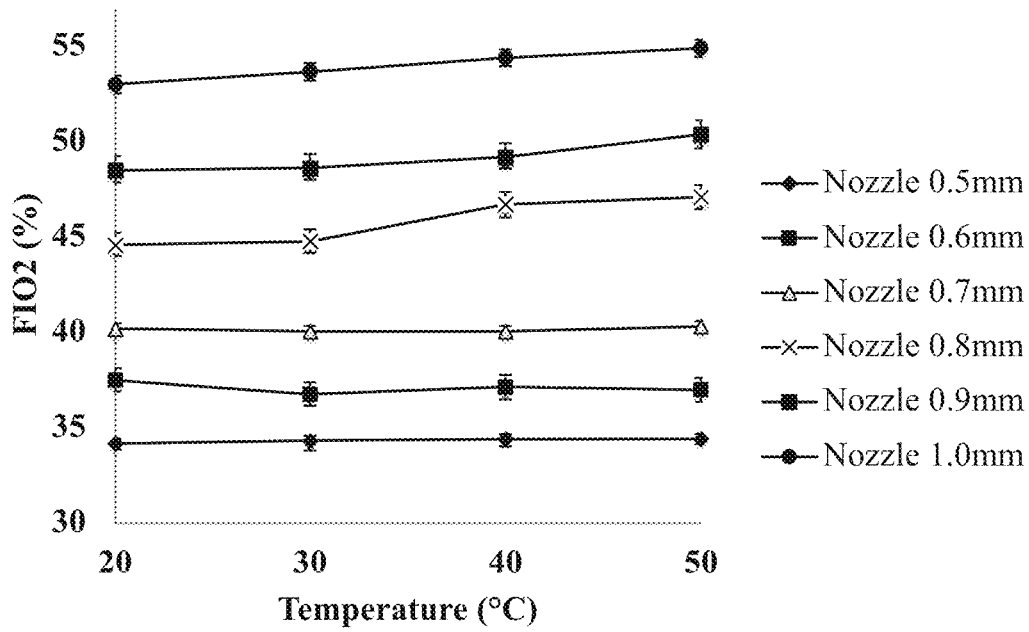
FIG. 9B is a graph illustrating a fraction of inspired oxygen (FiO2) as a function of a temperature, for a plurality of different nozzle sizes and a fixed outlet orifice diameter size, in accordance with at least some embodiments.

FIG. 9B is a graph 902 illustrating a fraction of inspired oxygen (FiO2) as a function of a temperature, for a plurality of different nozzle sizes and a fixed outlet orifice diameter size, in accordance with at least some embodiments.

Referring to FIG. 9B, the graph shows that the fraction of inspired oxygen (FiO2) that was observed in a mixture exiting an ambient air-oxygen blender having a nozzle diameter of 0.5 mm and an outlet orifice diameter of 2.0 mm increased very slightly with an increase in temperature from 20° C. to 50° C. The fraction of inspired oxygen (FiO2) that was observed in a mixture exiting an ambient air-oxygen blender having a nozzle diameter of 0.6 mm and an outlet orifice diameter of 2.0 mm decreased slightly with an increase in temperature from 20° C. to 50° C. The fraction of inspired oxygen (FiO2) that was observed in a mixture exiting an ambient air-oxygen blender having a nozzle diameter of 0.7 mm and an outlet orifice diameter of 2.0 mm was nearly unchanged with an increase in temperature from 20° C. to 50° C. The fraction of inspired oxygen (FiO2) that was observed in a mixture exiting an ambient air-oxygen blender having a nozzle diameter of 0.9 mm or 1.0 mm and an outlet orifice diameter of 2.0 mm increased slightly with an increase in temperature from 20° C. to 50° C. The largest effect of temperature was observed for an ambient air-oxygen blender having a nozzle diameter of 0.8 mm and an outlet orifice diameter of 2.0 mm. In this case, the fraction of inspired oxygen (FiO2) that was observed in the mixture exiting the ambient air-oxygen blender increased from 44.6%±0.6% to 47.1%±0.7% when the temperature increased from 20 to 50° C.

In at least some embodiments, an adjustable ambient air-oxygen blender may include an iris to provide an ability to reduce a cross sectional area of a nozzle.

Figures 10A, 10B:
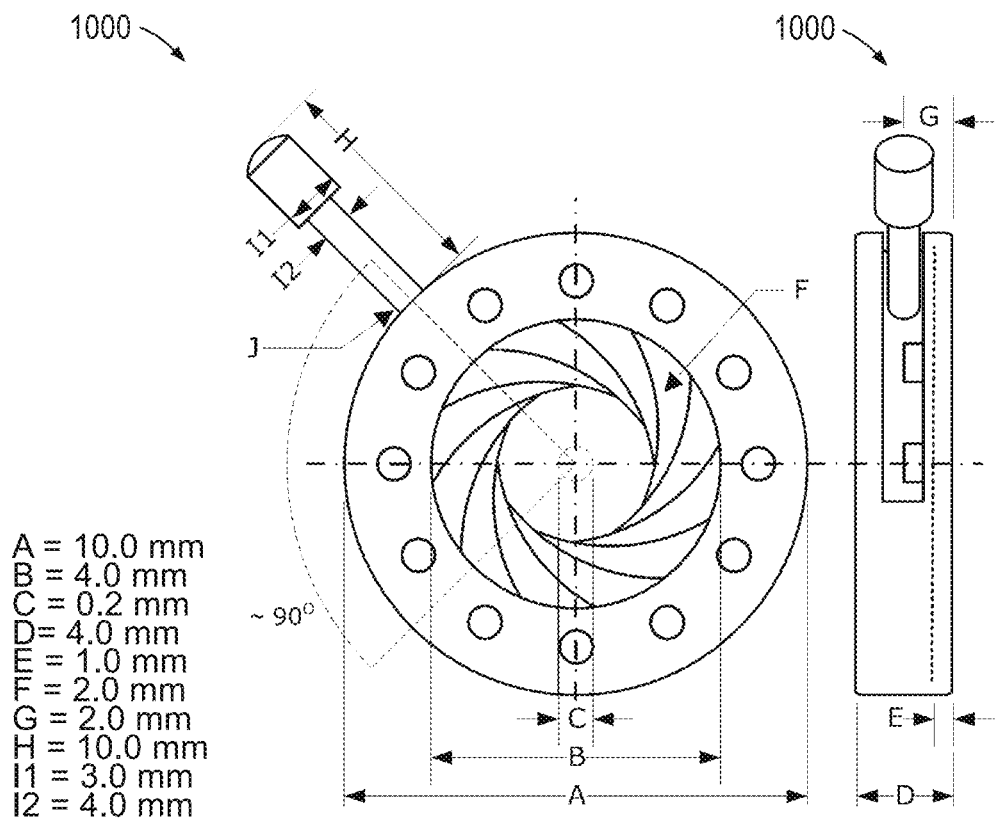
FIG. 10A is an end view of an iris with exemplary dimensions, in accordance with at least some embodiments.
FIG. 10B is a side view of the iris, in accordance with at least some embodiments.

FIG. 10A is an end view of an iris 1000, in accordance with at least some embodiments. The exemplary dimensions provided are only illustrative and not limiting.

FIG. 10B is a side view of the iris 1000, in accordance with at least some embodiments.

Referring to FIG. 10A, in accordance with at least some embodiments, the iris 1000 may include a frame 1002, an aperture 1004 and an actuator 1006. The frame 1002 may have an annular or any other suitable shape. The aperture 1004 may be coupled to the frame and may have a variable cross section that is controlled by the actuator 1006.

Figure 11:
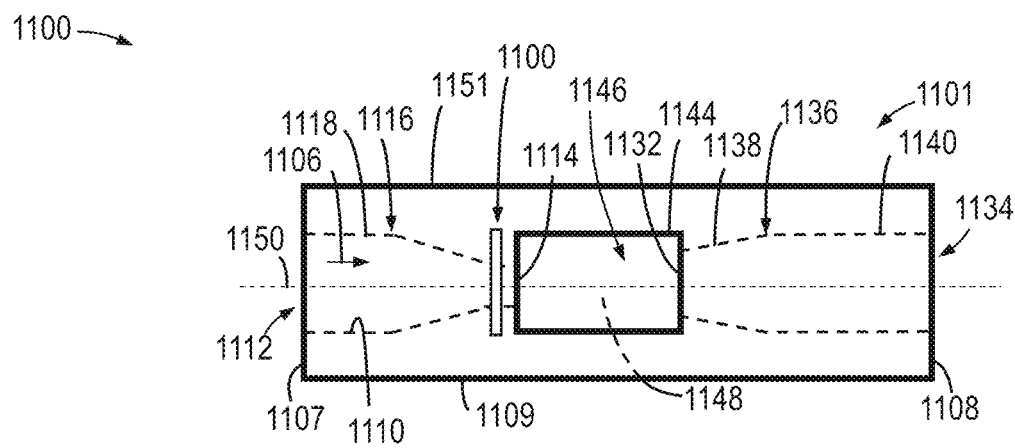
FIG. 11 is a perspective view of an adjustable ambient air-oxygen blender that includes the iris of FIGS. 10A-10B, in accordance with at least some embodiments.

FIG. 11 is a perspective view of an adjustable ambient air-oxygen blender 1100 that includes the iris 1000, in accordance with at least some embodiments.

Referring now to FIG. 11, in accordance with at least some embodiments, the adjustable ambient air-oxygen blender 1100 is similar to the fixed blender 501 of the adjustable ambient air-oxygen blender 500 (except where otherwise noted, like reference numerals that differ only in that one is preceded by the number "11" instead of by the number "5" are used to indicate like or similar elements) except that the adjustable ambient air-oxygen blender 1100 includes an iris 1000, which is disposed in fluid communication with and downstream of the oxygen inlet 1112

The variable aperture of the iris 1000 provides the ability to change the air-oxygen mixture. The mixture is thus adjustable without any need to stop the flow of oxygen, dismantle a blender from the system, connect a new blender and then resume the flow of oxygen.

Figure 12:
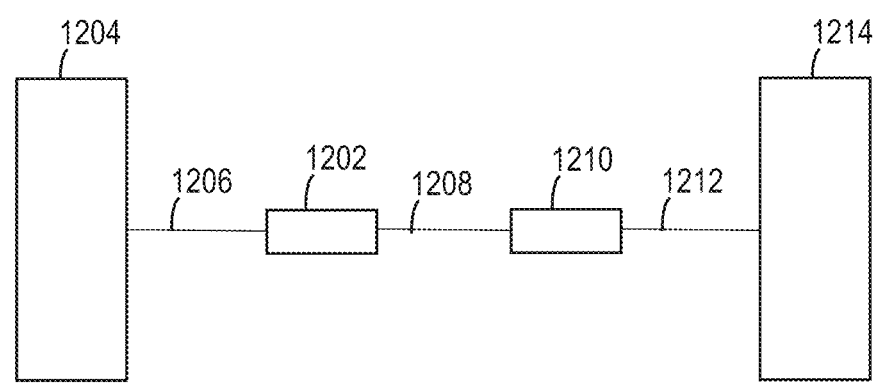
FIG. 12 is a schematic block diagram of a system that includes an adjustable ambient air-oxygen blender, in accordance with at least some embodiments.

FIG. 12 is a schematic block diagram of a bubble CPAP system 1200 that includes an adjustable ambient air-oxygen blender 1202, in accordance with at least some embodiments.

Referring to FIG. 12, in accordance with some embodiments, the adjustable ambient air-oxygen blender 1202 may comprise any of the adjustable ambient air-oxygen blender disclosed herein.

The system 1200 may further include a source 1204 of oxygen to be supplied to the adjustable ambient air-oxygen blender 1202 and to be mixed with ambient air. In at least some embodiments, the source 1204 may comprise a compressed oxygen tank with a flow meter.

The system 1200 may further include a tube or other gas line 1206 to supply the oxygen to the adjustable ambient air-oxygen blender 1202. The adjustable ambient air-oxygen blender 1202 may receive the oxygen and ambient air and provide an oxygen enriched air mixture thereof.

The system 1200 may further include a tube or other gas line 1208 to receive the mixture from the adjustable ambient air-oxygen blender 1202 and supply it to a nasal mask or other interface of a neonate (or other breathing apparatus) 1210.

The system 1200 may further include a tube or other gas line 1212 to receive expired air from the breathing apparatus 1210 and supply it to graduated water reservoir or other destination 1214. The tube or other gas line 1212 may be submerged in the graduated water reservoir or other destination 1214.

In at least some embodiments, the system 1200 may operate as follows. Compressed oxygen gas enters the adjustable ambient air-oxygen blender 1200, is forced to contract, and then passes through a small Venturi nozzle of the adjustable ambient air-oxygen blender 1200. Oxygen then exits from the Venturi nozzle into the air-entrainment chamber of the adjustable ambient air-oxygen blender 1200. The pressure-drop created by the Venturi effect provides the driving force to draw in ambient air and mix it with the oxygen stream. On the opposite side of the entrainment chamber from the Venturi nozzle, an orifice collects the mixed gas, which is supplied to the gas line 1208. The gas line 1208 supplies the mixed gas to the breathing apparatus 1210. The gas line 1212 receives expired air from the breathing apparatus 1210 and supplies it to graduated water reservoir or other destination 1214.

In at least some embodiments, any of the adjustable ambient air-oxygen blenders disclosed herein may have a rectangular cross-section of 7 mm×9 mm and a length of 73 mm or any other suitable configuration. The adjustable ambient air-oxygen blender may have two diametrically opposite rectangular-shaped air-entrainment ports, which may have a length of 15 mm and a width of 4.5 mm×15 mm or any other suitable configuration.

In at least some embodiments, adjustable ambient air-oxygen blenders disclosed herein may be fabricated using injection molding. In at least some embodiments, the following method may be used.

A four-piece negative stainless-steel mold may be used to produce a polymeric adjustable ambient air-oxygen blender. The four-piece mold may include two halves that produced a main body of the adjustable ambient air-oxygen blender and the air-entrainment window. The four-piece mold may further include side sections that are used to create the gas channels, the Venturi nozzle, and the orifice. Such a process allows adjustable ambient air-oxygen blenders with various Venturi nozzle and orifice sizes to be made simply by replacing the side pieces. It may also allow the adjustable ambient air-oxygen blenders to be fabricated in one injection step.

In at least some embodiments, the mold may be designed using 3D CAD software provided by SOLIDWORKS CORP located in Massachusetts. The mold may be machined from stainless steel.

In at least some embodiments, adjustable ambient air-oxygen blenders disclosed herein may be fabricated from polypropylene (Mw=250,000 g/mol), which may be provided by SCIENTIFIC POLYMER PRODUCTS, INC. located in New York. The polymer may be injected into the mold at 240° C. with the use of a benchtop injection molding machine, which may be provided by MEDIUM MACHINERY LLC located in Virginia in a one-step procedure. The fabricated part may be slow-cooled before removal from the mold. In some embodiments, three grams of polymer may be required per adjustable ambient air-oxygen blender.

It should be understood that the features disclosed herein can be used in any combination or configuration. Thus, in at least some embodiments, any one or more of the embodiments (or feature(s) thereof) disclosed herein may be used in association with any other embodiment(s) (or feature(s) thereof) disclosed herein. Similarly, in at least some embodiments, any one or more of the features disclosed herein may be used without any one or more other feature disclosed herein.

Also, some aspects may be embodied as one or more methods. The acts performed as part of the method may be ordered in any suitable way. Accordingly, embodiments may be constructed in which acts are performed in an order different than described, which may include performing some acts simultaneously.

Unless stated otherwise, terms such as, for example, "comprises," "has," "includes," and all forms thereof, are considered open-ended, so as not to preclude additional elements and/or features.

Also, unless stated otherwise, terms such as, for example, "a," "one," "first," are considered open-ended, and do not mean "only a", "only one" or "only a first", respectively.

Also, unless stated otherwise, the term "first" does not, by itself, require that there also be a "second."

Also, unless stated otherwise, the phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

In the foregoing specification, certain aspects have been described with reference to specific embodiments. However, one of ordinary skill in the art appreciates that various modifications and changes may be made without departing from the scope of the present invention as set forth in the claims below. Accordingly, the specification and figures are to be regarded in an illustrative rather than a restrictive sense, and all such modifications are intended to be included within the scope of present invention.

What is claimed is:

1. A gas blender apparatus for controllably blending a supply gas and an ambient gas, comprising:
    a first body part having a supply gas inlet that receives said supply gas and a supply gas exit nozzle in fluid communication with the supply gas inlet, the supply gas exit nozzle having a cross sectional area less than that of the supply gas inlet;
    a second body part configured and dimensioned to mechanically couple to said first body part and comprising a gas flow path for conducting a blended gas mixture of said supply gas and said ambient gas to an outlet of said apparatus;
    wherein said first and second body parts are moveable relative to one another and define a variable ambient gas entrainment port through which said ambient gas is entrained into an entrainment chamber in which said supply gas and said ambient gas are mixed to form said blended gas mixture; and
    wherein a relative position of said first and second body parts with respect to one another defines an area of said ambient gas entrainment port which is variable between an open position allowing entrainment of said ambient gas into said chamber and an occluded position preventing entrainment of said ambient gas into said entrainment chamber.

2. The gas blender apparatus of claim 1, said first and second body parts being configured and dimensioned so that the first and second body parts are slidably moveable with respect to one another along a longitudinal axis so as to increase or decrease said area of the ambient gas entrainment port and so as to correspondingly increase or decrease an amount of entrained ambient gas into said entrainment chamber.

3. The gas blender apparatus of claim 2, the relative position of said first and second body parts defining an axial dimension of said entrainment chamber.

4. The gas blender apparatus of claim 1, said first and second body parts being mechanically engaged with one another by mechanical threads and being movable with respect to one another by way of relative rotation of said threads in the first and second body parts.

5. The gas blender apparatus of claim 1, said first body part comprising a decreasing area gas flow channel that accelerates said supply gas as it approaches said supply gas exit nozzle.

6. The gas blender apparatus of claim 1, said first body part being coupled at said supply gas inlet to a source of supply gas including oxygen.

* * * * *